United States Patent [19]

Hoon et al.

[11] Patent Number: 6,057,105
[45] Date of Patent: May 2, 2000

[54] DETECTION OF MELANOMA OR BREAST METASTASIS WITH A MULTIPLE MARKER ASSAY

[75] Inventors: Dave S. B. Hoon; Andrew J. Conrad; Peter Schmid, all of Los Angeles, Calif.

[73] Assignee: NGI/Cancer Tech Company, LLC, Los Angeles, Calif.

[21] Appl. No.: 08/987,326

[22] Filed: Dec. 9, 1997

Related U.S. Application Data

[63] Continuation-in-part of application No. 08/406,307, Mar. 17, 1995, abandoned.
[51] Int. Cl.$^7$ .............................. C12Q 1/68; C12P 19/34; C07H 21/04; C07H 21/00
[52] U.S. Cl. ......................... 435/6; 435/91.1; 435/91.2; 536/23.5; 536/24.31; 536/24.33; 536/25.3
[58] Field of Search ............................. 435/6, 91.1, 91.2; 536/23.5, 24.31, 24.33, 25.3

[56] References Cited

FOREIGN PATENT DOCUMENTS

WO 90/09456  8/1990  WIPO.
WO 94/00603  1/1994  WIPO.

OTHER PUBLICATIONS

Lamerz et al In vivo vol. 7 pp. 607–614, 1993.
Kwon et al J. of Investigative Derm. vol. 100 No. 2 Suppl pp. 134S–140S, 1993.
Gaugler et al J. Exp Med. vol. 179 pp. 921–930, 1994.
Burchill, S.A. et al., "Detection of Epithelial Cancer Cells in Peripheral Blood by Reverse Transcriptase–Polymerase Chain Reaction," *British Journal of Cancer*, 71, 278–281 (1995).
Castaldo, Giuseppe, et al., "Lung Cancer Metastatic Cells Detected in Blood by Reverse Transcriptase–Polymerase Chain Reaction and Dot–Blot Analysis," *Journal of Clinical Oncology*, 15:11, pp. 3388–3393 (Nov. 1997).
Chi, Dorcas, D.J. et al., "Molecular Detection of Tumor--Associated Antigens Shared by Human Cutaneous Melanomas and Gliomas," *American Journal of Pathology*, 150:6, pp. 2143–2152 (Jun. 1997).
Datta, Yvonne H., et al., "Sensitive Detection of Occult Breast Cancer by the Reverse–Transcriptase Polymerase Chair Reaction," *Journal of Clinical Oncology*, 12:3, pp. 475–482 (Mar. 1994).
Doi, Fukashi, et al., "Detection of β–Human Chorionic Gonadotropin mRNA as a Marker for Cutaneous Malignant Melanoma," *Int. J. Cancer*, 65, pp. 454–459 (1996).
Hoon et al., "Detection of Metastatic Breast Cancer by β–hCC Polymerase Chain Reaction," *Int. J. Cancer (Pred. Oncol.)*, 69, 369–374 (1996).
Mellado, Begona, et al., "Detection of Circulating Neoplastic Cells by Reverse–Transcriptase Polymerase Chain Reaction in Malignant Melanoma: Association with Clinical Stage and Prognosis," *Journal of Clinical Oncology*, 14:7, pp. 2091–2097, (Jul. 1996).

Raj, Ganesh V., et al., "Utilization of Polymerase Chain Reaction Technology in the Detection of Solid Tumors," *Cancer*, 82:8, pp. 1419–1442 (Apr. 15, 1998
Sarantou, Terry et al., "Melanoma–Associated Antigens as a Messenger RNA Detection Markers for Melanoma," *Cancer Reserach*, 57, 1371–1376 (Apr. 1, 1997).
Smith, Barbara, et al., "Detection of Melanoma Cells in Peripheral Blood by Means of Reverse Transcriptase and Polymerase Chain Reaction," *The Lancet*, 338, pp. 1227–1229 (Nov. 16, 1991).
Stevens, Gerald Lester, et al., "Detection of Tyrosinase mRNA from the Blood of Melanoma Patients," *Cancer Epidemiology, Biomarkers & Prevention*, 5, pp. 293–296 (Apr. 1996).
Wang, Xiangning, M.D., et al., "Detection of Submicroscopic Lymph Node Metastases and Polymerase Chain Reaction in Patients with Malignant Melanoma," *Annuals of Surgery*, 220:6, pp. 768–774 (1994).
Cox, et al., "Tumor marker sensitivity: single versus multiple markers in patients with breast carcinoma," *Americal Journal of Clinical Pathology*, 94(4) p. 507, Oct. 1990, Abstract No. 77
Farghaly, Samir, A., "Tumor Markers in Gynecologic Cancer," *Gynbecological and Obstetric Investigation*, 34(2) pp. 65–72, 1992.
Mercer, Donald W., "Use of Multiple Markers to Enhance Clnical Utility," *Immunodiagnosis of Cancer, Immunology Series*, 53, pp. 39–54, 1990.
Sulitzeanu, D., et al., "Markers in Breast Cancer," *Isreal Journal of Medical Science*, 17(9–10), pp. 865–868, Sep. 1981.

*Primary Examiner*—Kenneth R. Horlick
*Assistant Examiner*—Jeffrey Siew
*Attorney, Agent, or Firm*—McCutchen, Doyle, Brown & Enerson, LLP; William E. Thomson, Jr.; Nina K. Srejovic

[57] ABSTRACT

Methods for detecting metastasis of melanoma and breast cancer cells, detecting subclinical metastasis, and monitoring treatment are disclosed. Kits for use in such methods also are disclosed. The methods provide for the detection of nucleic acids corresponding to multiple melanoma or breast cancer specific markers using template dependent amplification processes. Methods using multiple markers provide increased sensitivity over existing methods.

85 Claims, 1 Drawing Sheet

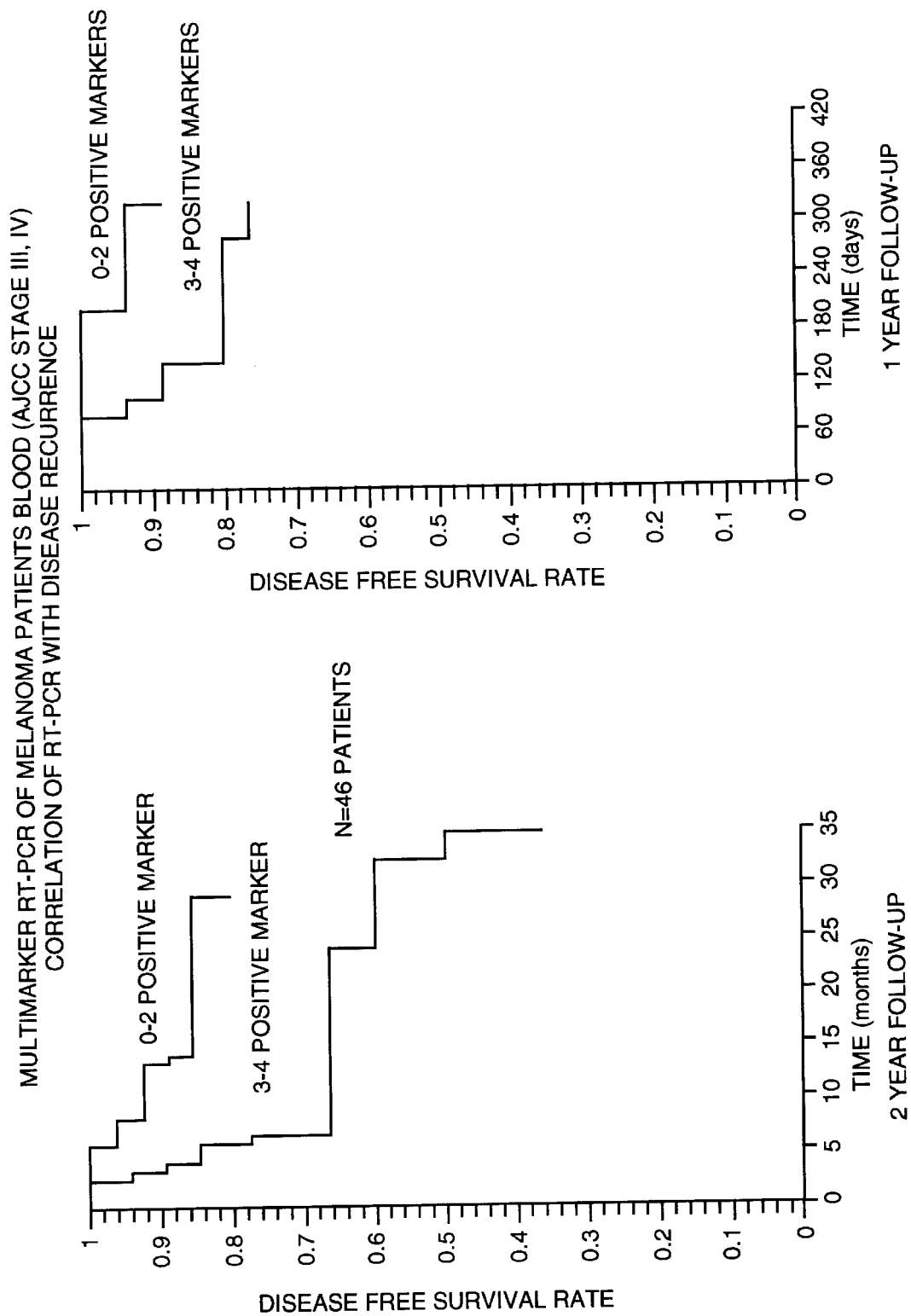

```
                              SEQUENCE LISTING

<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: primer
      sequence

<400> SEQUENCE: 1
gaagccggcc caggctcg                                                       18

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: primer
      sequence

<400> SEQUENCE: 2
ggagtcctca taggattggc tcc                                                 23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 3
ccaaggcaac ctcagccatg tc                                                  22

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: primer
      sequence

<400> SEQUENCE: 4
ctcgactcca cagtctggga cgact                                               25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 5
gtcatcttcc gtgtgcgcca                                                     20

<210> SEQ ID NO 6
<211> LENGTH: 25
<212> TYPE: DNA
<213> ORGANISM: Artificial Sequence
```

```
<220> FEATURE:
<223> OTHER INFORMATION: Description of Artificial Sequence: primer
      sequence

<400> SEQUENCE: 6
gtagcgacct cctcaggctc cttac                                          25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 7
ttggcagatt gtctgtagcc                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 8
aggcattgtg catgctgctt                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 9
gtctttatgc aatggaacgc                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 10
gctatcccag taagtggact                                                20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: primer
      sequence

<400> SEQUENCE: 11
tacctggtgg agagcggccg cctc                                           24

<210> SEQ ID NO 12
<211> LENGTH: 20
<212> TYPE: DNA
<213> ORGANISM: Artificial Sequence
<220> FEATURE:
```

-continued

```
<223> OTHER INFORMATION: Description of Artificial Sequence: primer
      sequence

<400> SEQUENCE: 12
agcgtcttcc ccatcagtgt                                                      20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 13
atgccaccct ggctgtggag aa                                                   22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 14
gggagtcggg atggacttgg aa                                                   22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 15
cagacacacg gtgaactatg g                                                    21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 16
gatcagcttc cactgttaga cg                                                   22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 17
cccgatgtgc tcctgaacca ga                                                   22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer
``` sequence

<400> SEQUENCE: 18
gctgacaccg acaagggca a                                          21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 19
ccaactcaac aggcaactac                                           20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 20
gatcataacg gaggaaggtc                                           20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 21
ggagcaatga tcttgatctt c                                         21

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 22
ccttcctggg catggagtcc tg                                        22

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: primer
      sequence

<400> SEQUENCE: 23
gctggaaccc tcactgggtt gcc                                       23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer
      sequence

```
<400> SEQUENCE: 24
cggccgaagg aacctgaccc ag                                          22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 25
ccaactcaac aggcaactac                                             20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 26
gatcataacg gaggaaggtc                                             20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 27
gtcctttggc gtcgtcctct                                             20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 28
atgggcgcat ttcggcttta                                             20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 29
caaactcaac aggcaactac                                             20

<210> SEQ ID NO 30
<211> LENGTH: 19
<212> TYPE: DNA
<213> ORGANISM: Artificial Sequence
<220> FEATURE:
```

```
<223> OTHER INFORMATION: Description of Artificial Sequence: primer
      sequence

<400> SEQUENCE: 30
agcgtcttcc catccgtgt                                              19
```

DETECTION OF MELANOMA OR BREAST METASTASIS WITH A MULTIPLE MARKER ASSAY

This application is a continuation-in-part of U.S. Ser. No. 08/406,307 filed Mar. 17, 1995, now abandoned. Priority is hereby claimed in the prior filed application. Some of the work described in this application was supported by grant numbers PO1 CA1038 and PO1 CA1039 from the National Cancer Institute and U.S. Army Breast Task Force.

FIELD OF THE INVENTION

The present invention relates generally to the field of cancer diagnostic techniques. In particular, the invention relates to the detection of genetic markers indicative of melanoma or breast cancer cells. In one example, detection of multiple markers is achieved by polymerase chain reaction assay.

DESCRIPTION OF THE RELATED ART

Cancers are one of the leading causes of disease, being responsible for 526,000 deaths in the United States each year (Boring et al., 1993). For example, breast cancer is the most common form of malignant disease among women in Western countries and, in the United States, is the most common cause of death among women between 40 and 55 years of age (Forrest, 1990). The incidence of breast cancer is increasing, especially in older women, but the cause of this increase is unknown. Malignant melanoma is another form of cancer whose incidence is increasing at a frightening rate, at least sixfold in the United States since 1945, and is the single most deadly of all skin diseases (Fitzpatrick, 1986).

One of the most devastating aspects of cancer is the propensity of cells from malignant neoplasms to disseminate from their primary site to distant organs and develop into metastases. Despite advances in surgical treatment of primary neoplasms and aggressive therapies, most cancer patients die as a result of metastatic disease. Animal tests indicate that about 0.01% of circulating cancer cells from solid tumors establish successful metastatic colonies (Fidler, 1993).

Thus, the detection of occult cancer cells in circulation is important in assessing the level of tumor progression and metastasis. Because subclinical metastasis can remain dormant for many years, monitoring of patients' blood for circulating tumor cells may prove advantageous in detecting tumor progression before metastasis to other organs occurs. Assessment of circulating tumor cells also would provide a rapid monitoring system to determine if a specific therapy is effective.

For example, recognition of metastases in tumor-draining lymph nodes (TDLN) now has been shown critical for patient management. It is known that between 25–30 per cent of breast cancer patients with node negative, localized disease will relapse within five years after operative intervention (Henderson et al., 1989). Accurate axillary staging of TDLN in detection of metastases has been an important factor for selecting patients for adjuvant therapy (NIH, 1992; Giuliano, et al., 1995; Giuliano, et al.. 1994). Several retrospective studies on breast cancer TDLN demonstrated that analysis of multiple sections of nodes shown to be tumor negative were found to have occult metastases (Bettelheim, et al., 1990; Chen et al., 1991; Neville et al., 1991). The identification of nodes with occult metastases were shown to significantly correlate to poorer prognosis (Bettelheim et al., 1990; Neville et al., 1991).

Previous tumor diagnostic techniques have focused on the detection of tumor associated antigens or on molecules released by tumor cells (Smart, 1990; Moertel et al., 1993; Stamey et al., 1989). At best, these assays only detect tumors with no indication of metastatic potential or tumor progression. In addition, such assays measure a single antigen whose release is often proportional to the size of the tumor and they cannot account for heterogeneity of individual markers in tumor lesions, both within individual patients or among patient groups.

The recent development of the PCR assay (Mullis and Faloona, 1987; Erlich, 1989) for detection of occult metastatic tumor cells in blood using specific markers has provided a new approach to assess tumor progression (Smith et al., 1991; Naito et al., 1991). In one study, circulating melanoma cells in blood were detected by PCR analysis using the tyrosinase gene marker (Smith et al., 1991). Seven melanoma patients with metastatic disease were analyzed, but only four were positive. Other studies using PCR have been used to detect circulating tumor cells in melanoma, as well as in breast, prostate and neuroblastoma cancer patients (Smith et al., 1991; Datta et al., 1994; Moreno et al., 1992; Naito et al., 1991). These studies, employing a single marker, were limited by their ability to discriminate cancer cells from normal cells also carrying the marker, thus reducing specificity and reliability. In addition, tumor heterogeneity has caused sensitivity problems where a single, specific marker has been employed.

As indicated above, tumors are notoriously heterogeneous, particularly in advanced stages of tumor progression (Morton et al., 1993; Fidler and Hart, 1982; Nowell, 1982; Elder et al., 1989; Bystryn et al., 1985). Although tumor cells within a primary tumor or metastasis all may express the same marker gene, the level of specific mRNA expression can Elder et al., 1989; Bystryn et al., 1985). Although tumor cells within a primary tumor or metastasis all may express the same marker gene, the level of specific mRNA expression can vary considerably (Elder et al., 1989). It is, therefore, necessary to develop a detection system that can cope with such heterogeneous targets.

Thus, despite the identification of melanoma and breast cancer markers, these markers cannot individually detect tumor cells in a highly specific and sensitive manner. This is due to the wide phenotypic diversity found in tumor cells at any one time and during disease progresion. There remains a need to develop a more sophisticated approach, that can accommodate such a biological heterogeneous situation in order to sensitively and specifically detect metastasis, monitor treatment, and diagnosis disease clinical stage.

SUMMARY OF THE INVENTION

The present invention seeks to overcome these and other drawbacks inherent in the prior art by providing sensitive and accurate methods for the detection of melanoma or breast cancer cells in a biological sample. The methods provide for the detection of melanoma or breast cancer cells in a biological sample by amplifying at least two nucleic acids from the sample, the nucleic acids being markers for melanoma or breast cancer cells.

The present invention comprises the following steps. A nucleic acid is extracted from a biological sample. Nucleic acid targets from at least two carcinoma marker genes are amplified if present. The presence or absence of the nucleic acid target is then detected.

In a preferred embodiment, the nucleic acid targets are amplified by contacting the nucleic acid with a first primer pair that hybridizes to a first melanoma or breast cancer marker nucleic acid. The primers are extended by polymerase to produce an amplification product. This process is repeated a sufficient number of times to permit detection of the amplification product. Finally, all steps are repeated with the same biological sample and a second primer pair that hybridizes to another melanoma or breast cancer marker nucleic acid.

In preferred embodiments, the method may further comprise preparing at least two pairs of primers complementary to regions of melanoma or breast cancer marker nucleic acids. In another embodiment, the method may further comprise preparing of primer pairs for at least three, four, five, six or even seven melanoma or breast cancer markers.

In preferred embodiments of the invention, the markers amplified and detected are selected from the group comprising tyrosinase, C-Met, TRP-1, MUC-18, p97, GalNAc, MART-1, and β-HCG, TRP-2 Cytokenatin 20 MAGE-1,2,3,4,12 and X. A preferred method of amplification is by reverse transcription and polymerase chain reaction (PCR). In one embodiment of die invention the PCR further comprises nested PCR.

In one embodiment, the nucleic acid is RNA. Preferably, the RNA extracted from a biological sample is total cellular RNA. In a preferred embodiment, the RNA is converted to DNA prior to amplification.

In certain embodiments of the invention, the biological sample is a body tissue or body fluid. In preferred embodiments, the body tissue is bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine. In a preferred embodiment, the biological sample is of human origin.

In preferred embodiments of the invention, the method includes separation of the amplification product by gel electrophoresis. In other embodiments, the method of separation is by chromatographic techniques. In a preferred embodiment of the invention, hybridization with a labeled probe permits identification of the amplification product following separation.

In further embodiments, the present invention encompasses a kit for use in detecting melanoma or breast cancer cells in a biological sample comprising pairs of primers for amplifying nucleic acids corresponding to the marker genes and containers for each of these primers. In preferred embodiments, the kit further comprises enzymes and reagents for the preparation of cDNA's and amplification thereof. In yet more preferred embodiments, the kit further comprises enzymes and reagents for radiochemical or chromophoric labeling of nucleic acids.

BRIEF DESCRIPTION OF THE DRAWINGS

FIG. 1 shows the correlation in one example between the number of markers detected by RT-PCR and disease recurrence.

DETAILED DESCRIPTION OF THE PREFERRED EMBODIMENTS

The present invention pertains to a sensitive, multimarker assay to detect occult melanoma or breast cancer cells in the blood of patients with or without clinical evidence of disease. This assay is designed to overcome limitations in existing technologies with respect to both sensitivity and specificity.

In its most general form, the instant invention comprises a method for identification of melanoma or breast cancer cells in a biological sample by amplifying and detecting nucleic acids corresponding to melanoma or breast cancer cell markers. The biological sample can be any tissue or fluid in which melanoma or breast cancer cells might be present. Preferred embodiments include bone marrow, lymph node aspirate, lymph node biopsy, spleen tissue, fine needle aspirate, skin biopsy or organ tissue biopsy. Other embodiments include samples where the body fluid is blood, lymph fluid, ascites, serous fluid, pleural effusion, sputum, cerebrospinal fluid, lacrimal fluid, stool or urine.

Nucleic acid used as template for amplification is isolated from cells contained in the biological sample according to standard methodologies. (Sambrook et al., 1989) The nucleic acid may be genomic DNA or fractionated or whole cell RNA. Where RNA is used, it may be desired to convert the RNA to a complementary cDNA. In a preferred embodiment, the RNA is whole cell RNA and is used directly as the template for amplification.

Pairs of primers that selectively hybridize to genes corresponding to specific markers are contacted with the isolated nucleic acid under conditions that permit selective hybridization. Once hybridized, the nucleic acid primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radio label or fluorescent label or even via a system using electrical or thermal impulse signals (Affymax technology, Bellus, 1994).

The foregoing process is conducted at least twice on a given sample using at least two different primer pairs specific for two different specific markers. Following detection, one may compare the results seen in a given patient with a statistically significant reference group of normal patients and melanoma or breast cancer patients. In this way, it is possible to correlate the number and kind of markers with various clinical states or disease prognosis.

(i) Melanoma-Specific or Breast Cancer-Specific Markers

While the present invention exemplifies several markers, any marker that is correlated with the presence or absence of melanomas or breast cancer may be used. A marker, as used herein, is any proteinaceous molecule (or corresponding gene) whose production or lack of production is characteristic of a melanoma or breast cancer cell. Depending on the particular set of markers employed in a given analysis, the statistical analysis will vary. For example, where a particular combination of markers is highly specific for melanomas or breast cancer, the statistical significance of a positive result will be high. It may be, however, that such specificity is achieved at the cost of sensitivity, i e., a negative result may occur even in the presence of melanoma or breast cancer. By the same token, a different combination may be very sensitive, i.e., few false negatives, but has a lower specificity.

As new markers are identified, different combinations may be developed that show optimal function with different ethnic groups or sex, different geographic distributions, different stages of disease, different degrees of specificity or different degrees of sensitivity. Marker combinations may also be developed, which are particularly sensitive to the effect of therapeutic regimens on disease progression. Patients may be monitored after surgery, hypothermia, immunotherapy, cytokine therapy, gene therapy, radiotherapy or chemotherapy, to determine if a specific therapy is effective.

One particularly useful combination of markers is tyrosinase and p97. Human tyrosinase is an essential enzyme which regulates the production of melanin (Nordlund et al., 1989; Hoon et al., 1993), a group of brown or black pigments in the skin and eyes of humans. More specifically, tyrosinase catalyzes the conversion of tyrosine to Dopa and of Dopa to dopaquinone. p97, also known as melanotransferrin, is a cell surface sialoglycoprotein that bears some sequence homology to transferring (Brown et al., 1981; Rose et al., 1986). Like transferring, p97 binds iron, thereby being implicated in iron metabolism.

There are many other markers that may be used in combination with these, and other, markers. For example, β-human chorionic gonadotropin (β-HCG). β-HCG is produced by trophoblastic cells of placenta of pregnant woman and is essential for maintenance of pregnancy at the early stages (Pierce et al., 1981; Talmadge et al., 1984). β-HCG is known to be produced by trophoblastic or germ cell origin tumors, such as choriocarcinoma or testicular carcinoma cells (Madersbacher et al., 1994; Cole et al., 1983). Also ectopic expression of β-HCG has been detected by a number of different immunoassays in various tumors of non-gonadal such as breast, lung, gastric, colon, and pancreas, etc. (McManus et al., 1976; Yoshimura et al., 1994; Yamaguchi et al., 1989; Marcillac et al., 1992; Alfthan et al., 1992). Although the function of β-HCG production in these tumors is still unknown, the atavistic expression of β-HCG by cancer cells and not by normal cells of non-gonadal origin suggests it may be a potentially good marker in the detection of melanoma and breast cancer (Tormey et al., 1977; Tormey et al., 1975).

Another exemplary example of a marker is glycosyltransferase β-1,4-N-acetylgalacto-saminyltransferase (GalNAc). GalNAc catalyzes the transfer of N-acetylgalactosamine by β1,4 linkage onto both gangliosides GM3 and GD3 to generate GM2 and GD2, respectively (Nagata, et al., 1992; Furukawa et al., 1993). It also catalyzes the transfer of N-acetylgalactosamine to other carbohydrate molecules such as mucins. Gangliosides are glycosphingolipids containing sialic acids which play an important role in cell differentiation, adhesion and malignant transformation. In melanoma, gangliosides GM2 and GD2 expression, are often enhanced to very high levels and associated with tumor progression including metastatic tumors (Hoon et al., 1989; Ando et al., 1987; Carubia et al., 1984; Tsuchida et al., 1987a). Gangliosides are also highly expressed in breast cancer cells. The gangliosides GM2 and GD2 are immunogenic in humans and can be used as a target for specific immunotherapy such as human monoclonal antibodies or cancer vaccines (Tsuchida et al., 1987b; Irie 1985).

GalNAc mRNA may be used as a marker of GM2 and GD2 expression and consequently a marker of either melanoma or breast cancer cells. GalNAc is generally not expressed in normal lymphocytes, epithelial cells, melanocytes, connective tissue or lymph node cells. If detected, it is in very low levels.

Cytokeratin 20 (CK 20) has been found to be a marker of breast cancer cells. Burchill et al., 1995. Primers that may be used to amplify the cytokeratin 20 marker are: sense: CAG ACA CAC GGT GAA CTA TGG (SEQ ID NO: 15) and antisense: GAT CAG CTT CCA CTG TTA GAC G (SEQ ID NO: 16). If these primers are used the product size is 370 bp.

Other markers contemplated by the present invention include cytolytic T lymphocyte (CTL) targets. MAGE-3 is a marker identified in melanoma cells and breast carcinoma. MAGE-3 is expressed in many melanomas as well as other tumors and is a (CTL) target (Gaugler et al., 1994). MAGE-1, MAGE-2, MAGE-4, MAGE-6, MAGE-12, and MAGE-X are other members of the MAGE gene family which are useful markers. MAGE-1 gene sequence shows 73% identity with MAGE-3 and expresses an antigen also recognized by CTL (Gaugler et al., 1994). MART-1 is another potential CTL target (Robbins et al., 1994) and may also be included in the present invention.

MUC-18 is another marker that is useful in the identification of melanoma cells (Lehmann et al., 1989; Lehmann et al., 1987). MUC-18 is a cell surface glycoprotein that is a member of the immunoglobulin superfamily and possesses sequence homology to neural cell adhesion molecules (NCAM).

Other members of the immunoglobulin superfamily of adhesions molecules associated with the development of melanoma metastasis (Denton et al., 1992) may be utilized in the present invention. Another preferred embodiment of the invention, includes cell adhesion molecules associated with other metastatic diseases, such as carcinoembryonic antigen (CEA) (Johnson, 1991).

Other breast or skin cancer associated proteins and their corresponding nucleic acids may also be utilized in the present invention. Preferred examples include melanoma antigen gp75, also known as TRP-1 (Vijayasardahi et al., 1990), high molecular weight melanoma antigen (Natali et al., 1987) and cytokeratin 19 (CK 19) (Datta et al., 1994), and CK 20 (Burchill, et al., 1995). This list is not intended to be exhaustive, but merely exemplary, for the type and number of potential markers which may be used in the present invention.

Other proteins and their corresponding nucleic acids related to the melanin synthesis pathway may be used as markers, such as tyrosinase related protein 1 (TRP-1) and 2 (TRP-2) and members of the pMel 17 (gp100) gene family (Kwon et al., 1993).

Preferred embodiments of the invention involve many different combinations of markers for the detection of melanoma and breast cancer cells. Any marker that is indicative of neoplasia in breast cells or melanocytes may be included in this invention. However, preferred embodiments include combinations of tyrosinase, MAGE-3, MUC-18, p97, β-HCG, GalNAc, MART-1 and MAGE-1. Other preferred embodiments include the combination tyrosinase, MART-1, MAGE-3 and TRP-1 for melanoma or the combinations of C-Met, GalNAc, β-HCG, MAGE-3, MAGE-2, and CK 20 for breast cancer. Particularly useful are the combinations C-Met, GalNAc, MAGE-3 and CK 20; C-Met, MAGE-2, MAGE-3 and CK 20; or MAGE-X, MAGE-2, MAGE-3 and CK 20. Table 1, as well as the examples disclosed herein, partially represent useful combinations of markers which may be employed for the detection of melanoma or breast cancer cells.

TABLE 1

Preferred Multiple Marker Combinations

| Tyrosinase | p97 | MUC-18 | MAGE3 | β-HCG | GalNAc | MAGE1 |
|---|---|---|---|---|---|---|
| *Table 1A. Combinations of Six or Seven Multiple Markers* | | | | | | |
| + | + | + | + | + | + | + |
| + | + | + | + | + | + | − |
| + | + | + | + | + | − | + |
| + | + | + | + | − | + | + |
| + | + | + | − | + | + | + |
| + | + | − | + | + | + | + |
| + | − | + | + | + | + | + |
| − | + | + | + | + | + | + |
| *Table 1B. Combinations of Five Multiple Markers* | | | | | | |
| + | + | + | + | + | − | − |
| + | + | + | + | − | − | + |
| + | + | + | − | − | + | + |
| + | + | − | − | + | + | + |
| + | − | − | + | + | + | + |
| − | − | + | + | + | + | + |
| − | + | + | + | + | + | − |
| + | + | + | + | − | + | − |
| + | + | − | + | − | + | + |
| + | − | + | − | + | + | + |
| − | + | − | + | + | + | + |
| + | − | + | + | + | + | − |
| − | + | + | + | + | − | + |
| + | + | + | − | + | + | − |
| + | + | − | + | + | + | − |
| + | − | + | + | − | + | + |
| − | + | + | − | + | + | + |
| + | + | + | − | + | − | + |
| − | + | + | + | − | + | + |
| + | + | − | + | + | − | + |
| − | + | + | + | − | + | + |
| *Table 1C. Combinations of Four Multiple Markers* | | | | | | |
| + | + | + | + | − | − | − |
| + | + | + | − | − | − | + |
| + | + | − | − | − | + | + |
| + | − | − | − | + | + | + |
| − | − | − | + | + | + | + |
| − | − | + | + | + | − | − |
| + | + | + | − | − | + | − |
| + | + | − | − | + | − | + |
| + | − | − | + | − | + | + |
| − | − | + | − | + | + | + |
| − | + | − | + | + | + | − |
| + | − | + | + | + | − | − |
| − | + | + | + | − | − | + |
| + | + | − | + | − | − | + |
| + | − | + | − | − | + | + |
| + | − | + | − | + | + | − |
| − | + | − | − | + | + | + |
| − | − | + | + | + | − | − |
| − | + | + | + | − | + | − |
| + | + | − | − | + | + | − |
| − | − | + | + | − | + | + |
| − | + | + | − | + | + | − |
| + | + | − | + | + | − | − |
| + | − | + | + | − | − | + |
| − | − | + | − | − | + | + |
| *Table 1D. Combinations of Three Multiple Markers* | | | | | | |
| − | − | − | − | + | + | + |
| − | − | − | + | + | + | − |
| − | − | + | + | + | − | − |
| − | + | + | + | − | − | − |
| + | + | + | − | − | − | − |
| + | + | − | − | − | − | + |
| + | − | − | − | − | + | + |
| − | − | − | + | + | − | + |
| − | − | + | + | − | + | − |
| + | + | − | + | − | − | − |
| + | − | + | − | − | − | + |
| − | + | − | − | + | + | − |
| + | − | − | − | + | + | − |
| + | − | + | − | − | − | + |
| − | + | − | − | − | + | + |
| + | + | − | − | + | − | − |
| − | − | + | − | + | + | − |
| + | − | − | + | − | + | − |
| − | + | + | − | − | − | + |
| + | − | − | + | + | − | − |
| − | + | − | − | + | − | + |
| + | − | − | − | + | − | + |
| − | + | + | − | − | + | − |
| + | − | + | + | − | − | − |
| − | − | + | + | − | − | + |
| + | + | − | − | − | + | − |
| + | − | − | + | − | − | + |
| − | − | + | − | + | − | + |
| − | + | − | + | − | − | + |
| + | − | − | − | + | + | − |
| − | + | − | + | + | − | − |
| *Table 1E. Combinations of Two Multiple Markers* | | | | | | |
| − | − | − | − | − | + | + |
| − | − | − | − | + | + | − |
| − | − | − | + | + | − | − |
| − | − | + | + | − | − | − |
| − | + | + | − | − | − | − |
| + | + | − | − | − | − | − |
| + | − | − | − | − | − | + |
| − | − | − | + | − | + | − |
| − | − | + | − | + | − | − |
| − | + | − | + | − | − | − |
| + | − | + | − | − | − | − |
| − | + | − | − | − | − | + |
| + | − | − | − | − | + | − |
| − | − | − | + | − | − | + |
| − | − | + | − | − | + | − |
| − | + | − | − | + | − | − |
| + | − | − | + | − | − | − |
| − | − | + | − | − | − | + |
| − | + | − | − | + | − | − |
| + | − | − | − | + | − | − |

+ markers include in the combination; − markers not included.

(ii) Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

In most cases, it will be preferable to synthesize desired oligonucleotides. Suitable primers can be synthesized using commercial synthesizers, such as those supplied by Applied Biosystems (Foster City, Calif.) using methods well known to those of ordinary skill in the art. Where double-stranded primers are desired, synthesis of complementary primers is performed separately and the primers mixed under conditions permitting their hybridization.

Selection of primers is based on a variety of different factors, depending on the method of amplification and the specific marker involved. For example, the choice of primer will determine the specificity of the amplification reaction. The primer needs to be sufficiently long to specifically hybridize to the marker nucleic acid and allow synthesis of amplification products in the presence of the polymerization agent and under appropriate temperature conditions. Shorter primer molecules generally require cooler temperatures to form sufficiently stable hybrid complexes with the marker nucleic acid and may be more susceptible to non-specific hybridization and amplification.

Primer sequences do not need to correspond exactly to the specific marker sequence. Non-complementary nucleotide fragments may be attached to the 5' end of the primer with the remainder of the primer sequence being complementary to the template. Alternatively, non-complementary bases can be interspersed into the primer, provided that the primer sequence has sufficient complementarily, in particular at the 3' end, with the template for annealing to occur and allow synthesis of a complementary DNA strand.

In preferred embodiments, primers may be designed to hybridize to specific regions of the marker nucleic acid sequence. For example, GC rich regions are favored as they form stronger hybridization complexes than AT rich regions. In another example, primers are designed, solely, to hybridize to a pair of exon sequences, with at least one intron in between. This allows for the activity of a marker gene to be detected as opposed to its presence by minimizing background amplification of the genomic sequences and readily distinguishes the target amplification by size.

Primers also may be designed to amplify a particular segment of marker nucleic acid that encodes restriction sites. A restriction site in the final amplification product would enable digestion at that particular site by the relevant restriction enzyme to produce two products of a specific size. Any restriction enzyme may be utilized in this aspect. This added refinement to the amplification process may be necessary when amplifying a marker nucleic acid sequence with close sequence similarity to other nucleic acids. Alternatively, it may be used as an added confirmation of the specificity of the amplification product.

(iii) Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and U.S. Pat No. 4,800,159, and in Innis et al., 1990, each of which is incorporated herein by reference in its entirety. Briefly, in PCR, two primer sequences are prepared which are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated. Preferably a reverse transcriptase PCR amplification procedure may be performed in order to quantify the amount of mRNA amplified. Methods of reverse transcribing RNA into cDNA are well known and described in Sambrook et al., 1989. Alternatively, preferred methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the marker sequence, each pair will bind to opposite complementary strands of the marker such that they abut. In the presence of a ligase, the two probe pairs will link to form a single unit. By temperature cycling, as in PCR, bound ligated units dissociate from the marker and then serve as "target sequences" for ligation of excess probe pairs. U.S. Pat. No. 4,883,750 describes a method similar to LCR for binding probe pairs to a marker sequence.

Qbeta Replicase, described in PCT Application No. PCT/US87/00880, may also be used as still another amplification method in the present invention. In this method, a replicative sequence of RNA which has a region complementary to that of a marker is added to a sample in the presence of an RNA polymerase. The polymerase will copy the replicative sequence which can then be detected.

An isothermal amplification method, in which restriction endonucleases and ligases are used to achieve the amplification of marker molecules that contain nucleotide 5'-[alpha-thio]-triphosphates in one strand of a restriction site may also be useful in the amplification of nucleic acids in the present invention. Walker et al., 1992, incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) involves annealing several probes throughout a region targeted for amplification, followed by a repair reaction in which only two of the four bases are present. The other two bases can be added as biotinylated derivatives for easy detection. A similar approach is used in SDA. Marker specific sequences can also be detected using a cyclic probe reaction (CPR). In CPR, a probe having a 3' and 5' sequences of nonspecific DNA and middle sequence of specific RNA is hybridized to DNA which is present in a sample. Upon hybridization, the reaction is treated with RNaseH, and the products of the probe identified as distinctive products which are released after digestion. The original template is annealed to another cycling probe and the reaction is repeated.

Still another amplification methods described in British Patent Application No. 2,202,328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g, biotin) and/or a detector moiety (e.g., enzyme). In the latter application, an excess of labeled probes are added to a sample. In the presence of the marker sequence, the probe binds and is cleaved catalytically. After cleavage, the marker sequence is released intact to be bound by excess probe. Cleavage of the labeled probe signals the presence of the marker sequence.

Other nucleic acid amplification procedures include transcription-based amplification systems (TAS), including nucleic acid sequence based amplification (NASBA) and 3SR. Kwoh et al., 1989; Gingeras et al., PCT Application WO 88/10315, incorporated herein by reference in their entirety. in NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has marker specific sequences. Following polymerization, DNA/RNA hybrids are digested with RNase H while double stranded DNA molecules are heat denatured again. In either case the single stranded DNA is made fully double stranded by addition of second marker specific primer, followed by polymerization. The double-stranded DNA molecules are then multiply transcribed by a polymerase such as T7 or SP6. In an isothermal cyclic reaction, the RNAs are reverse transcribed into double-stranded DNA, and transcribed once against with a polymerase such as T7 or SP6. The resulting products, whether truncated or complete, indicate marker specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of his process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a marker single-stranded DNA ("ssDNA") followed by transcription of many RNA copies of the sequence. This scheme is not cyclic, i e., new templates are not produced from the resultant RNA transcripts. Other amplification methods include "race" and "one-sided PCR." Frohman, M. A., 1990 and Ohara et al., 1989, each incorporated herein by reference in their entirety.

Methods based on ligation of two (or more) oligonucleotides in the presence of nucleic acid having the sequence of the resulting "di-oligonucleotide", thereby amplifying the dioligonucleotide, may also be used in the amplification step of the present invention. Wu et al., 1989, incorporated herein by reference in its entirety.

(iv) Separation Methods

Following amplification, it may be desirable to separate the amplification product from the template and the excess primer for the purpose of determining whether specific amplification occurred. In a preferred embodiment, amplification products are separated by agarose, agarose-acrylamide or polyacrylamide gel electrophoresis using standard methods. See Sambrook et al., 1989. In a preferred embodiment, the gel is a 2 k agarose gel.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

Alternatively, separation may be unnecessary. These methods may be collectively termed Sequencing By Hybridization or SBH (Cantor et al., 1992; Drmanac & Crkvenjakov, U.S. Pat. No. 5,202,231). Development of certain of these methods has given rise to new solid support type sequencing tools known as sequencing chips. The utility of SBH in general is evidenced by the fact that U.S. Patents have been granted on this technology.

SBH can be conducted in two basic ways, often referred to as Format 1 and Format 2 (Cantor et al., 1992). In Format 1, oligonucleotides of unknown sequence, generally of about 100–1000 nucleotides in length, are arrayed on a solid support or filter so that the unknown samples themselves are immobilized (Strezoska et al., 1991; Drmanac & Crkvenjakov, U.S. Pat. No. 5,202,231). Replicas of the array are then interrogated by hybridization with sets of labeled probes of about 6 to 8 residues in length.

In Format 2, a sequencing chip is formed from an array of oligonucleotides with known sequences of about 6 to 8 residues in length (Southern, WO 89/10977; Khrapko et al., 1991; Southern et al., 1992). The nucleic acids of unknown sequence are then labeled and allowed to hybridize to the immobilized oligos. In another embodiment, hybridization may be detected by electrical or thermal impulse signals (Affymax Technology, Bellus, 1994).

In a preferred method, however, visualization is achieved indirectly. Following separation of amplification products, a lsheled. nucleic acid srobe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In a particularly preferred embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

(vi) Clinical Stages of Malignant Melanoma

Cancers are staged according to a well-defined, elaborate progressive scale, developed by the American Joint Committee on Cancer.

Malignant melanomas can arise in any skin area that contains melanocytes, but body moles, also called pigmented nevi, are particularly vulnerable. Although some moles, especially those on the face and torso, originate in pigment cells, they sometimes contain little pigment and are light in color. All moles are initially benign tumors of varying shape, but it is significant to note that about 20 to 30 percent of all melanomas begin in the pigment cells of moles.

Caught early, melanoma is very often curable. On the other hand, melanomas that are not detected until they have invaded even a few millimeters of the deeper layers of skin have a much poorer prognosis. The five-year survival rate varies considerably depending on stage level. For Stage I and Stage II melanoma, the five-year survival rate is over 80%. However, for Stage IV the survival rate is less that 20% (AJCC).

A simplified summary of the scale, developed by the American Joint Committee for the Staging of melanoma is presented in Table 2.

TABLE 2

Staging of Melanoma

| | |
|---|---|
| Stage I: | Primary site, small tumor<br>Negative lymph nodes<br>No detectable metastases |
| Stage II: | Invasion beyound primary site<br>Lymph nodes negative may have one positive<br>No Detectable distant metastases |
| Stage III: | Tumors at regional skin or subcutaneous sites,<br>Primarily located to lymph nodes. |
| Stage IV: | Tumor of any size<br>Lymph nodes either positive or negative<br>Distant metastases to multiple sites |

Metastasis to a distal organ may or may not result in secondary metastasis to other organs. Since subclinical tetastasis can remain dormant for many years, monitoring of a patient's blood for circulating tumor cells may be helpful in detecting tumor progression before clinically evident metastases to other organs are detected by physical examination or conventional imaging technique (Xray, CATscan, or MRI).

(vii) Clinical Stages of Breast Cancer

Many factors appear to influence the chances of surviving breast cancer. Early detection and treatment are the most important. The overall five-year survival rate is about 75 percent for white women and about 63 percent for black women. This rises to nearly 90 percent for women with Stage I or II cancer that is treated while the cancer is confined to the breast (Scanlon and Strax, 1986).

A simplified summary of the scale, developed by the American Joint Committee for the Staging of Breast Cancer in 1982, is presented in Table 3.

TABLE 3

Staging of Breast Cancers

| | |
|---|---|
| Stage I: | Small tumor (less than 2 cm or .78 inches)<br>Negative lymph nodes<br>No detectable metastases |
| Stage II: | Tumor greater than 2 cm but less than 5 cm<br>Lymph nodes negative<br>or |

TABLE 3-continued

Staging of Breast Cancers

| | |
|---|---|
| | Tumor less than 5 cm across<br>Lymph nodes positive<br>No detectable distant metastases |
| Stage III: | Large tumor (greater than 5 cm)<br>or<br>Tumor of any size with invasion of skin or chest wall or "grave signs"<br>or<br>Associated with positive lymph nodes in the collarbone area<br>but<br>No detectable distant metastases |
| Stage IV: | Tumor of any size<br>Lymph nodes either positive or negative<br>distant metastases |

(viii) Kit Components

All the basic essential materials and reagents required for detecting melanoma or breast cancer cells in a biological sample, may be assembled together in a kit. This will generally comprise of the preselected primers for two, or more, particular specific markers. Also included may be enzymes suitable for amplifying nucleic acids including various polymerases (RT, Taq, etc.), deoxynucleotides and buffers to provide the necessary reaction mixture for amplification.

Such kits will generally comprise, in suitable means, distinct containers for each individual reagent and enzyme as well as for each marker primer pair. Preferred pairs of primers for amplifying nucleic acids correspond to the genes tyrosinase, MART-1, MAGE-1, MAGE-2, MAGE-3, MAGE-4, MAGE-12, MAGE-X, TRP-1, TRP-2, MUC-18, C-Met, GalNAc, CK 20, β-HCG and p97.

Kits of the present invention, also will typically include a means for containing the reagents in close confinement for commercial sale such as, e.g., injection or blow-molded plastic containers into which the desired reagent are retained. Other containers suitable for conducting certain steps of the disclosed methods also may be provided.

(ix) Monitoring Treatment

The methods disclosed herein are useful in monitoring the treatment of melanoma and breast cancer. The methods may be performed immediately before, during and after treatment to monitor treatment success. The methods also should be performed at intervals, preferably every three to six months, on disease free patients to insure treatment success. Preferably, blood from patients is tested for metastatic cells.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

DETECTION OF MULTIPLE MARKER RNA EXPRESSION IN MELANOMA CELLS

A. Materials and Methods (i) Melanoma Cell Lines

Melanoma cell lines M10, M12, M24, M101, Mke, Mst, Mmu, Mka, and Mkn were established and characterized at the John Wayne Cancer Institute (JWCI). Cells were grown in RPMI 1640 plus 10W fetal calf serum (heat-inactivated) (Gemini, Calabasas, Calif.) plus penicillin and streptomycin (GIBCO, Long Island, N.Y.) in T75 cm² flasks. Adherent cell lines were routinely passaged by trypsinization every 3–4 days (Hoon et al., 1993). For PCR studies, cell lines were used when 75–85 k confluent.

(ii) Blood Preparation and RNA Extraction

Peripheral blood lymphocytes (PBL) were obtained from the buffy coat of 15 ml of blood from healthy normal donors. The cells were washed by centrifugation for 5 min.

Total cellular RNA was extracted using the UltraSpec isolation system (Biotecx, Houston, Tex.) or Tri-Reagent isolation system (Molecular Research Center, Inc., Cincinnati Ohio) as described by the manufacturer. For UltraSpec, the cells were lysed in 2 ml of UltraSpec RNA reagent by repetitive pipetting and placed in ice for 5 min. Four hundred µl of chloroform was added and mixed rigorously for 15 sec and placed on ice for 5 min. The solution was centrifuged at 12,000×g at 4° C. for 15 min. The upper phase was transferred into a RNAse-free eppendorf tube, 1 volume of isopropanol was added and the solution was precipitated at 4° C. for 10 min. The tube was centrifuged at 12,000 g at 4° C. for 20 min. The sample was washed with 70% ethanol, dried, and resuspended in 50 µl of DEPC (diethylpyrocarbonate)-treated Tris-EDTA (TE) buffer.

For Tri-Reagent, the cells were lysed in 1 ml of Tri-Reagent by repetitive pipetting and were placed on ice for 5 min. Two hundred µl of chloroform was added and mixed vigorously for 15 sec and incubated at room temperature for 5 min. The solution was then centrifuged at 12,000×g at 4° C. for 15 min. The upper aqueous phase was transferred into an RNAse-free eppendorf tube, equal volume of isopropanol was then added and the nucleic acid was allowed to precipitate at room temperature for 10 min. The tube was then centrifuged as 12,000×q at 4° C. for 10 min. The sample was washed twice with 70% ethanol, vacuum-dried, and resuspended in 10 mM Tris-HCI with 1 ml EDTA solution (pH 7.4). The concentration of total RNA was determined usinq a Beckman spectrophotometer. One µg of total RNA was used in the PCR assay to detect mRNA.

All extraction procedures for each specimen were carried out separately in a designated laminar flow hood under sterile conditions to avoid potential RNA cross-contamination. PCR reagent set up and post-PCR gel electrophoresis were carried out in separate rooms and buildings to avoid potential RNA cross-contamination.

(iii) Oligonucleotide Primers and Probes

Oligonucleotide primers were synthesized and purified at the Molecular Biology Institute Core Facility, UCLA. Oligonucleotide 5'- and 3'-primers for individual genes were as follows: MAGE-3 primers were 5'-GAAGCCGGCCCAGGCTCG-3' (SEQ ID NO: 1) and 5'-GGAGTCCTCATAGGATTGGCTCC-3' (SEQ ID NO: 2); MUC-18 primers were 5'-CCAAGGCAACCTCAGCCATGTC-3' (SEQ ID NO: 3) and 5'-CTCGACTCCACAGTCTGGGACGACT-3' (SEQ ID NO: 4); MUC-18 nested primers were 5'-GTCATCTTCCGTGTGCGCCA-3' (SEQ ID NO: 5) and 5'-GTAGCGACCTCCTCAGGCTCCTTAC-3' (SEQ ID NO: 6); tyrosinase were 5'-TTGGCAGATTGTCTGTAGCC-3' (SEQ ID NO: 7) and 5'-AGGCATTGTGCATGCTGCTT-3' (SEQ ID NO: 8); tyrosinase nested primers were 5'-GTCTTTATGCAATGGAACGC-3' (SEQ ID NO: 9) and 5'-GCTATCCCAGTAAGTGGACT-3' (SEQ ID NO: 10); and p97 primers were 5'-TACCTGGTGGAGAGCGGCCGCCTC-3' (SEQ ID NO: 11) and 5'-AGCGTCTTCCCCATCAGTGT-3' (SEQ ID NO: 12). The amplification products of MAGE-3, MUC-18, MUC-18 "nested," tyrosinase, tyrosinase "nested" and p97 were 423, 437, 262, 284, 207 and 286 bp, respectively.

(iv) Reverse Transcription and Polymerase Chain Reaction (RT-PCR)

The RT-PCR assay was performed as previously described with some modifications (Hoon et al., 1993). An oligo (dT) 15 primer was employed for the reverse transcription step, to produce cDNA and guarantee its amplification over genomic DNA. The reverse transcription (RT) mixture consisted of 4 µl 25 mM MgCl$_2$, 2 µl 10× RT buffer, 4 µl 10 mM dinucleotide triphosphate mixture, 0.5 µl RNAs in (40 U/µl), 1 µl AMV reverse transcriptase (9 U/µl), and 1 µl oligo(dT) 15 primer (1.5 µg/µl). Three µg of sample RNA was added to the RT mixture and H$_2$O was added to bring the volume up to 20 µl. All reagents were obtained from Promega (Madison, Wis.). The reaction was incubated at 42° C. for 2 hr, 99° C. for 5 min, and on ice for 5 min.

The PCR mixture consisted of 10 µl 10× PCR buffer (Perkin Elmer Cetus, Norwalk, Conn.), 8 µl 10 mM dNTPs mixture, 1 µl 5' primer (100 pmol/µl), 1 µl 5'- and 3'-primer, 0.5 µl AmpliTaq 5 U/µl (100 mM Tris-HCl, pH 8.3, 500 mM KCl, 15 mM MgCl$_2$, 0.01% gelatin, Perkin Elmer Cetus) and 20 µl of RT mixture. Sterile, double-distilled H$_2$O was added to the mixture to bring it up to 100 Hl. The mixture was overlaid with mineral oil. The PCR conditions were set up as follows: 95° C. for 5 min followed by 95° C. for 70 sec, 52° C. for 70 sec, 72° C. for 70 sec for 40 cycles, and 72° C. for 10 min extension time and soaked at 4° C. The PCR reaction was performed in an OmniGene temperature cycler (Hybaid, Middlesex, England).

To assess nested primers to a particular gene the PCR mixture after completion through the PCR cycling was added (10 µl) to 10 µl of 10× PCR buffer, 8 µl of 10 mM dNTPs, 1 µl of 5' nested primer (100 pmol/µl), 1 µl of 3'-nested primer (100 pmol/µl) and 0.5 µl of AmpliTaq polymerase (5 U/µl). The volume of the mixture was brought up to 100 µl. The PCR cycling was perrformed as for the first reaction except the annealing temperature was 55° C. The preparation of PCR mixture for the temperature cycler was carried out in a designated PCR room in a specified laminar flow hood.

The PCR amplification product was detected by electrophoresis on a 2% agarose gel (GIBCO BRL, Grand Island, N.Y.) and visualized by ethidium bromide staining under ultra violet light. An φX174RF DNA/Hae III fragment DNA ladder (BRL) was used as a size reference marker for all assays.

B. Results

The screening process involved examining 10 established melanoma cell lines (10$^6$ cells/line) and 39 normal PBL (10$^7$ cells/blood draw) as controls. In Table 4, the expression of these markers is shown for melanoma cells and PBL. A positive reaction was considered as a visible specific PCR amplification product by gel electrophoresis stained with ethidium bromide.

TABLE 4

PCR analysis of melanoma marker genes

| Marker gene | Melanoma cell lines | PBL |
|---|---|---|
| Tyrosinase | 9/10 | 0/39 |
| p97 | 10/10 | 0/39 |

TABLE 4-continued

PCR analysis of melanoma marker genes

| Marker gene | Melanoma cell lines | PBL |
|---|---|---|
| MAGE-3 | 8/10 | 0/39 |
| MUC-18 | 10/10 | 2/39 |

RNA was extracted from melanoma and PBL and assessed for expression of individual markers by PCR. Data presented as positive cell lines or PBL over total number of specimens assessed. Positive PCR refers to PCR amplification product assessed by gel electrophoresis.

All four markers were transcribed in all the melanoma lines, except for MAGE-3. A melanoma cell line expressing all four markers would produce cDNA PCR products of size; 284 base pairs (bp), 286 bp, 423 bp and 437 bp (tyrosinase, p97, MAGE-3 and MUC-18 respectively) as observed after electrophoresis through an agarose gel with ethidium bromide staining and compared with DNA size markers. In one melanoma cell line, tyrosinase expression by PCR was negative; however, when nested PCR for tyrosinase was performed tyrosinase gene expression was detected. There was no detection of melanoma markers in PBL from 39 normal donors, except two donors which were positive for MUC-18 gene transcription. These individuals were tested multiple times from separate blood draws and always remained positive for MUC-18. This indicated they were not false positive results due to PCR contamination or contamination from normal tissue during blood drawing.

In all assays, MUC-18 nested primer PCR was performed; this procedure increased the sensitivity to allow verification and amplification of weak bands produced by PCR with only MUC-18 primers. Melanoma cell lines and PBL were tested at least twice to verify specificity. Respective controls in each assay included samples with positive RNA for the gene being assessed, PCR reagents and primers without RNA, human tumor cell lines which were negative for individual gene expression, and β-actin gene expression.

MAGE-1, a gene family member of MAGE-3, also was tested and found to be transcribed in less than 50% of the melanoma cell lines. It was decided not to use this marker for melanoma, since MAGE-3 is more highly expressed in melanomas and MAGE-3 is usually found when MAGE-1 is expressed (Gaugler et al., 1994). Expression of both genes were not detected in PBL from normal volunteer donors.

EXAMPLE II

SENSITIVITY OF MULTIPLE MELANOMA MARKERS

A. Materials and Methods

RNA was isolated and quantitated from melanoma cell lines positive for individual markers. Specific marker PCR analysis was then carried out on serial diluted RNA as described in Example I.

(i) Southern Blot Analysis

After electrophoresis of PCR amplification products, agarose gels were transferred overnight onto nitrocellulose membrane (Schleicher & Schull, Keene, N.H.) with 20× SSC buffer as previously described. The cDNA was then crosslinked onto the membrane and hybridized overnight with a digoxigenin labelled probe (Morisaki et al., 1992). After hybridization, the membrane was washed in 2× SSC, 0.1% SDS for 10 min. at room temperature and then in 0.1× SSC, 0.1% SDS for 30 min. at 68° C. to remove nonspecific binding (Sambrook et al., 1989). Specific binding was detected using anti-digoxigenin, alkaline phosphatase conjugated antibody as described by the manufacturer (Genius Kit; Boehringer Mannheim, Indianapolis, Ind.). Tyrosinase probes were either prepared, full-length from PCR cDNA products using the outermost PCR oligonucleotide primers, or 2K bp probes were Eco R1 digested from plasmids containing the tyrosinase gene sequence (Kwon et al., 1987). All other probes used in Southern blotting, were prepared from PCR cDNA products using the outermost oligonucleotide primers.

Gel electrophoresis and Southern blotting also was performed automatically using the Automated Electrophoresis System, National Genetics, Inc. and U.S. Pat. No. 5,279,721. See above.

B. Results

In general, all markers could be detected at picogram levels of RNA by visual examination of gel-electrophoresed PCR amplification products stained with ethidium bromide. RNA from melanoma cell lines were diluted in a series from 1 to $10^{-9}$ μg and assessed for markers tyrosinase, p97, MUC-18, and MAGE-3. Sensitivity varied for individual lines with different levels of gene expression. In general, mRNA for p97, MUC-18, and MAGE-3 was detected around 10–100 pg by PCR. Tyrosinase mRNA could be detected at 10–100 fg by PCR.

Specificity of the amplification products was demonstrated by Southern blotting with respective specific probes (tyrosinase, p97). Sensitivity of the PCR assay could be enhanced 10- to 100-fold using PCR followed by probe blotting. Nested PCR for tyrosinase enhanced detection levels 10–100 fold above PCR for tyrosinase. However, nested PCR for MUC-18 enhanced results about 10-fold compared to standard PCR for MUC-18.

EXAMPLE III

DETECTION OF MELANOMA CELLS MIXED WITH PBL IN VITRO

A model system mimicking circulating melanoma cells in blood was developed. In this assay, system $10^7$ normal PBL were mixed with serial dilutions of melanoma cells ($10^6$ to 1 cell) and assessed by PCR for individual gene markers. The PCR amplification products were then assessed by ethidium bromide staining of gels and by Southern blot analysis. RT-PCR amplification was also performed on RNA extracted from $10^7$ PBL and 10 melanoma cells, as controls. Southern blot analysis performed for tyrosinase verified the specificity of the PCR amplification product and demonstrated enhanced sensitivity. Materials and methods were as described in Examples I and II.

Gel electrophoresis or nested primers analysis demonstrated that melanoma cells could be detected at about 1 cell in $10^7$ PBL for tyrosinase, p97 and MUC-18. PBL controls were negative for individual markers in both gel staining and Southern blot analysis and in both standard and nested PCR. Specific dilutions of melanoma cells, were also analysed, in 50 million PBL and demonstrated that about 1–5 melanoma cells could be detected in 50 million PBL with nested primer tyrosinase PCR followed by probinq with tyrosinase cDNA.

To demonstrate the sensitivity and reproducibility of detecting 1 melanoma cell in million PBL, a Poisson distribution analysis was carried out. In 8 of 11 samples, a positive PCR amplification product developed by tyrosinase PCR was detected by gel electrophoresis. The level of detection was enhanced >90% when tyrosinase nested PCR primers or Southern blot analysis with tyrosinase probe was performed.

EXAMPLE IV

ASSESSMENT OF CIRCULATING MELANOMA CELLS IN PATIENTS BLOOD

A. Materials and Methods (i) Patients

All melanoma patient with complete documented physical and medical histories were accrued from JWCI. Melanoma patients studied were AJCC (American Joint Committee on Cancer) stage I, II, III and IV. Patients assessed were NED (no evidence of clinical disease), AWD (alive with clinical disease) or EXP (expired during follow-up). The accrual and study of patients was carried out in a double-blind fashion. The patients' disease status was not known to the individual running the PCR assay nor the analyzer of the PCR data. Clinical disease status was documented at the time of blood drawing and again at 8–15 month follow-up period. PCR data results were not known to individuals recording the patient status during the follow-up period.

Fifteen ml of blood was obtained from patients and collected 5 in sodium citrate tubes. All blood was drawn in the John Wayne Cancer Clinic using the same procedure. Blood was drawn after written consent was obtained from the patient. The protocol for the study was approved by the Saint John's Hospital and John Wayne Cancer Institute Human Subjects Committee. Tubes were centrifuged for 20 min at 2000×g. The buffy coat was carefully removed and diluted in double distilled water. The cells were washed by centrifugation for 5 min. All other materials and methods were performed as described in Example I and II.

(ii) Protocol

Materials and methods were as described in Examples I and II. PBL from melanoma patients were examined using an optimized PCR assay detection system. The protocol was as follows: PCR assays were performed to detect mRNA transcripts of tyrosinase, p97, MAGE-3, and MUC-18. All melanoma patients were subjected to all four tests. If the sample was negative for tyrosinase or MUC-18, nested PCR was performed with respective primers. If the PBL specimen was negative in the PCR assay for tyrosinase nested primers and p97 markers, then Southern blot analysis would be performed with respective probes. PBLs negative for all the markers and tests were considered as true negatives.

Initially, cells isolated by Ficoll-hypaque gradient centrifugation were compared to buffy coat isolated nucleated cells from blood. In the analysis, buffy coat isolated cells were better for the detection of circulating melanoma cells in blood by PCR.

B. Results

A summary of the analysis of blood specimens by PCR using multiple markers, as assessed by ethidium bromide stained gels, is shown in Table 5. The greatest number of positive patients was observed with MUC-18 (73%), with tyrosinase (59%), p97 (54%) and MAGE-3 (10%) identifying few. Analysis with nested primers of tyrosinase versus tyrosinase primers significantly increased the number of positive patients from 2 to 57. Further analysis of p97-negative and tyrosinase-negative patients with respective specific probes significantly increased the number of positive patients. The most significant increase was observed by Southern blotting with the p97 probe. Six patients were positive for all four markers. All six patients were stage IV.

TABLE 5

Analysis of melanoma patients using multiple marker PCR assay
Number of patients positive

| Assays | p97 | tyrosinase | MAGE-3 | MUC-18 |
|---|---|---|---|---|
| PCR | 16 | 2 | 12 | 80 |
| Nested PCR | — | 57 | — | 87 |
| cDNA blot | 49 | 12 | — | — |
| Total patients | 65 | 71 | 12 | 87 |

The PCR analyses were correlated with disease stage and status (AWD & EXP, NED) of patients. The follow-up time for clinical status after blood drawing for PCR analysis was 8–15 months. In the study, there were 4, 18, 32, and 66 Stage I, II, III, and IV patients, respectively. The majority of the patients in individual Stages II to IV were PCR positive. Table 6.

TABLE 6

PCR positive patients in correlation to Disease status patient status

| AJCC Stage | AWD & EXP | NED |
|---|---|---|
| I | NP | 1/4 |
| II | NP | 16/18 |
| III | 5/6 | 23/26 |
| IV | 46/48 | 17/18 |
| Total positive | 51/54 (94%) | 57/66 (86%) |

The detection of PCR markers was correlated with the Breslow thickness and Clark level of the primary melanoma, after it had been surgically removed. The latter two factors play a role in determining the patients prognosis (Breslow, 1970; Morton et al., 1993). Breslow thickness has been shown to correlate very well with disease progression. Breslow thickness was divided into subgroups of 0.75 mm or less, >0.75 mm to 1.49 mm, >=21. 5 mm to >3.0 mm and, 3.0 mm. However, there was no significant correlation of Breslow thickness and detection of PCR markers. Although the majority of the patients were either Clarkts level 3 or 4, no significant pattern was observed for Clark's level and number of positive PCR markers. Neither the number of tumor-positive regional lymph nodes nor the sites of distal metastases significantly correlated with the number of positive PCR markers.

The lack of correlation between primary melanoma Breslow thickness and Clark's level with the number of PCR positive markers may be due to the fact that tumor progression is no longer dependent on these initial pathological parameters of the primary tumor once it has been removed.

EXAMPLE V

STATISTICAL ANALSIS

To assess the difference between using tyrosinase alone as a marker and using tyrosinase, MUC-18, p97 and MAGE-3 together, a coefficient in level for small sample proportion analysis was performed. Assessment of significance of disease stage to PCR data that was analyzed is summarized below:

| n = 120 | Stage I =   | 4  | NED = 65 |
|---------|-------------|----|----------|
|         | Stage II =  | 18 | AWD = 38 |
|         | Stage III = | 32 | EXP = 17 |
|         | Stage IV =  | 66 |          |

Of the 120 patients, 49 tested negative for tyrosinase. 42 of these tested Positive for at least one of the other three markers (MUC-18, P97, MAGE-3). This improvement is statistically significant at the 99% confidence level. It can therefore, be concluded that the four marker PCR assay is more sensitive than the single marker (tyrosinase) assay.

Next, an attempt to correlate a patient's disease stage (I, II, III, or IV) and the number of positive markers (0–4) was undertaken. Table 7 shows the breakdown.

TABLE 7

Number of PCR markers correlated to stage and disease status

| Disease | Patients Number of positive markers | | | | | Total |
|---------|---|---|---|---|---|---|
| Stage   | 0 | 1 | 2 | 3 | 4 | Patients |
| I       | 3 | 0 | 0 | 1 | 0 | 4   |
| II      | 2 | 6 | 5 | 5 | 0 | 18  |
| III     | 4 | 5 | 15 | 8 | 0 | 32 |
| IV      | 3 | 15 | 23 | 18 | 7 | 66 |
| Total   | 12 | 26 | 43 | 32 | 7 | 120 |

Positive markers refer to detection of tyrosinase, p97, MUC18 and MAGE-3 by either PCR, nested PCR or Southern blotting.

The results show a positive correlation between stage and the number of positive markers, p=0.0025, i.e., as stage increases, the proportion of positive markers also seems to increase.

In the follow-up period after blood drawing, patients were divided into those with clinical evidence of disease progression and those with no evidence. The number of patients positive for 0 to 4 PCR markers was correlated to disease progression. The relationship between progression and the number of positive markers also was assessed. Analysis showed that there was a significant correlation (p<0.05) between number of positive markers and disease progression. Table 8.

TABLE 8

Number of PCR markers correlated to progression of disease

|                | 0 pos | 1 pos | 2 pos | 3 pos | 4 pos | TOTAL |
|----------------|-------|-------|-------|-------|-------|-------|
| No Progression | 9     | 13    | 32    | 17    | 2     | 73    |
| Progression    | 3     | 13    | 11    | 15    | 5     | 47    |
| TOTAL          | 12    | 26    | 43    | 32    | 7     | 120   |

Thus, although tyrosinase has been used as a marker in a previous report, the studies disclosed herein indicate that tyrosinase alone is not always sensitive in detecting circulating melanoma cells. The use of more than one marker can verify the presence of occult melanoma cells and significantly increase the sensitivity of detecting melanoma cells that express few or no copies of tyrosinase mRNA. The study demonstrated that using four markers was significantly better than tyrosinase alone. In addition, the number of markers detected in individual patients correlated, significantly, with stage and disease progression. This higher expression of individual marker genes indicates, that there is an increase in the heterogeneity of tumor cells or an increase in the number of cells in circulation, at advance stages of disease.

Overall, the level of detection was similar for tyrosinase and p97 markers. MUC-18 marker was the most frequently detected whereas, MAGE-3 was the lowest. Although MAGE-3 is expressed in cell lines and biopsies in higher frequency, the number of mRNA copies in a single tumor cell is likely to be very low. This may be related to the state of the cell or clonal phenotype during circulation in the blood.

EXAMPLE VI

DETECTION OF β-HCG mRNA EXPRESSION IN MELANOMA CELLS

A. Materials and Methods (i) Melanoma Cell Lines

Twenty-four melanoma cell lines were established and characterized at John Wayne Cancer Institute as previously described (Hoon et al., 1991). Cell lines were cultured and passaged as described in Example I.

(ii) RNA Extraction

Total cellular RNA was extracted, isolated and purified using Tri-Reagent according to the manufacturer's protocol (Molecular Research Center, Inc. Cincinnati, Ohio) and described in detail in Example I. Cells from melanoma lines were lightly trypsinized and collected from tissue culture flasks Biopsy specimens if cryopreserved were rapidly thawed and kept in a ice water bath. Tumor biopsies were kept in a ice water bath when being minced. All RNA extraction was carried out in a sterile designated laminar flow hood with RNase free labware. Purified RNA was quantitated and assessed for purity by UV spectrophotometry.

(iii) Oligonucleotide Primers and Probes

Oligonucleotide primers were synthesized and purified at the Molecular Biology Institute Core Facility, UCLA. The β-HCG primer sequences were as follows: 5' primer was 5'-ATGCCACCCTGGCTGTGGAGAA-3' (SEQ ID NO: 13) and the 3' primer was 5'-GGGAGTCGGGATGGACTTGGAA-3' (SEQ ID NO: 14). The RT-PCR cDNA product was 367 bp. The 5' primer has only one mismatch with the -luteinizing hormone (LH, see below) while the 3' primer is homologous to both β-HCG AND β-LH coding regions. A full-length, PCR product, amplified from β-HCG DNA, was used a probe for Southern blot analysis.

The primer sequences for β-HCG/LH receptors were 5' primer, 5'-CCCGATGTGCTCCTGAACCAGA-3' (SEQ ID NO: 17); and 3' primer, 5'-GCTGACACCGACAAGGGGCAA-3' (SEQ ID NO: 18). The RT-PCR cDNA product for β-HCG/LH receptors was 496 bp. The β-actin primer sequences were as follows: 5' primer was 5'-GGAGCAATGATCTTGATCTTC-3' (SEQ ID NO: 21) and the 3' primer was 5'-CCTTCCTGGGCATGGAGTCCTG-3' (SEQ ID NO: 22). The RT-PCR product was 201 bp. The tyrosinase and MAGE-3 primers were the same as described in Example I.

(iv) RT-PCR Assay

The RT-PCR assay was carried out as previously described (Morisaki et al., 1992, and in Example I). Briefly, reverse transcription was carried out with oligo (dT)$_{15}$ primer and AMV reverse transcriptase with 5 μg of RNA and incubated for 2 hr at 42° C. and 99° C. for 5 min. The RT-PCR conditions were set up as follows: 95° C. for 5 min followed by 95° C. for 1 min, 65° C. for 1 min. 72° C. for 1 min, and 72° C. for 10 min for final primer extension sequence and performed in an OmniGene thermocycler (Hybaid, Middlesex, England).

(v) Restriction Digestion

β-HCG is a gonadotropin hormone composed of an α- and β-subunit (Hoon, et al., 1996, Fiddes et al., 1979; Boorstein et al., 1982). The amino acid sequence of α-HCG is essentially indistinguishable from those of the other human gonadotropin hormones, such as follicle-stimulating, luteinizing, and thyroidstimulating hormones (Fiddes et al., 1979; Pierce et al., 1981). However, the β-HCG subunit is different amongst the other hormone subunits except for the β-LH subunit; they share 82% common amino acid sequence (Talmadge et al., 1984). The β-subunit of HCG to data has been shown to consist of cluster of 6 related genes linked closely to the β-LH single gene (Bo et al., 1992). Since the β-HCG and β-LH are highly homologous it is not possible to design a primer sequence absolutely specific to β-HCG.

However, the β-HCG PCR cDNA product has a unique Sty I restriction site that is not present in the β-LH PCR cDNA product. Digestion of PCR products with this enzyme allows β-HCG to be distinguished from β-LH. RT-PCR cDNA product was incubated with 10× NEBuffer 3 (New England BioLabs, Beverly, Mass.) and sty I (10 U/ml) (New England Biolabs) and the mixture was incubated overnight at 37° C. The endonuclease digested product mixture was run on a 2% agarose gel and stained with Etbr. β-HCG RT-PCR cDNA product digested with Sty I produces a 271 and 96 bp band. If no digestion occurred the reaction was repeated at least twice to confirm.

(vi) Southern Blotting

RT-PCR cDNA products run on a 2% agarose gel were denatured and transferred overnight onto nylon membrane (Micron Separations, Inc.) as previously described in Example II. β-HCG cDNA probe was prepared by PCR, purified and digoxigenin labelled as described in Example II.

B. Results

Assessment of β-HCG expression in cells by molecular techniques has been difficult because of the sequence homologies of both α and β subunits to related hormones. The terminal end of the β-chain subunit chain was chosen as a target for RT-PCR since it had the most significant differences compared to other related hormone β-chain subunits.

Initially 24 established human melanoma cell lines derived from different anatomical sites were assessed to determine if they expressed β-HCG chain. Oligo dT$_{(15)}$ priming was carried out to assess only poly A mRNA of β-HCG. Of the 24 cell lines tested by RT-PCR, 16 of 24 produced a specific cDNA product of the correct size (367 bp) as verified by Etbr gel staining.

β-actin was run on all samples as an internal control to verify RNA yield and efficiency of the RT-PCR assay. Each assay had a negative control consisting of RT-PCR reagents alone without RNA and a positive control for β-HCG. Southern blot analysis of PCR cDNA product with the β-HCG probe showed that three of the cell lines negative by Etbr staining had a specific cDNA band. However, one cell line in which the Etbr staining was questionable showed no specific band on Southern blot analysis. Overall 18 out of 24 cell lines were positive (75%) for β-HCG marker expression.

To further verify β-HCG marker expression, endonuclease restriction digestion with Sty I was carried out on the RT-PCR cDNA products. All cDNA products digested, produced two bands, 271 bp and 96 bp as observed on Etbr gels, indicative of β-HCG marker. These digested products were further verified by Southern blot analysis with β-HCG cDNA probe.

EXAMPLE VII

DETECTION OF β-HCG MRNA EXPRESSION IN MELANOMA TUMOR BIOPSS SPECIMENS

A. Materials and Methods (i) Melanoma Tumor Biopsy Specimens and Blood Preparation Melanoma tumor biopsy specimens that were defined by histopathology as malignant melanoma were assessed. Melanoma biopsies were obtained from primary lesions and from multiple anatomical sites of metastatic lesions from different patients. Specimens were immediately frozen or processed as received from the operating room. In this study liquid nitrogen cryopreserved and fresh tumor biopsies from surgery were assessed. On obtaining melanoma biopsies non-melanoma tissue was carefully dissected away from normal tissue under sterile conditions in a laminar flow hood.

PBL were obtained from 25 normal male and female volunteer donors and the buffy coat was collected for RNA isolation as described in Example I. All other techniques including RT-PCR, Southern blotting and restriction enzyme digests were as described in Example VI.

Normal axillary lymph node tissue that was assessed as histopathology negative for tumor was obtained from melanoma and breast cancer patients undergoing elective surgery. Axillary lymph nodes were assessed by histopathology for malignancy by standard conventional hematoxylin and eosin (H & E) staining.

B. Results

Melanoma primaries and metastases have been shown to contain infiltrating immune cells (Cochran and Hoon, 1987). To be certain that β-HCG mRNA was being expressed by the tumor cells and not a product of infiltrating lymphoid cells, nucleated blood cells were also analysed for expression of β-HCG mRNA. PBL from 25 normal volunteer donors were analysed by RT-PCR but no evidence of β-HCG expression was observed, even after Southern blot analysis (except in one individual who was positive in a second blood draw).

Five lymph nodes from two breast and melanoma patients, were found to be negative by H & E staining and by RT-PCR and Southern blotting.

Both cryopreserved and fresh biopsy tissue were anaylsed by histopathology and by RT-PCR, restriction digestion and Southern blotting. Out of 40 patients, 38 were identified, as melanoma positive by histopathology, while 16 were identified as positive by RT-PCR for β-HCG marker. In other words, an estimated 42% of melanoma biopsies were β-HCG positive. All specimens that were found to be melanoma negative by histopathology, were also negative for β-HCG marker expression. The detection of β-HCG mRNA was much weaker in melanoma biopsy tissues as compared to melanoma cell lines. This detected lower gene activity may be due to the heterogeneity of tumors, variability of host physiologic regulation of β-HCG, or simply the dilution of RNA by normal cell infiltrate.

There was no significant difference in β-HCG mRNA detection between cryopreserved and fresh biopsy specimens. β-actin expression was detected in all specimens, thus verifying the 30 integrity of the mRNA and the PCR assay.

EXAMPLE VIII

A COMPARISON OF β-HCG MRNA EXPRESSION WITH OTHER MELANOMA MARKERS

A. Materials and Methods (i) Surgical Specimens

Axillary lymph node tissue was taken after elective surgery of TDLN from seven melanoma patients. TDLN were assessed by histopathology for malignancy by standard conventional hematoxylin and eosin (H & E) staining. β-HCG mRNA expression was compared with tyrosinase and MAGE-3 mRNA expression by RT-PCR. All other materials and methods were as described in Example VI.

B. Results

Out of eight tumor-draining lymph nodes (TDLN) (from seven melanoma patients) five were positive for β-HCG expression, six for tyrosinase and three for MAGE-3. In two patients, none of the markers were detected.

TABLE 9

Analysis of β-HCG expression in melanoma TDLN

| TDLN | Path | β-actin | β-HCG EtBr | β-HCG S. Blot | β-HCG Sty I | Tyr | MAGE3 |
|------|------|---------|-----------|--------------|------------|-----|-------|
| 1 | + | + | − | + | + | + | − |
| 2 | + | + | − | + | + | + | − |
| 3 | + | + | − | − | + | + | + |
| 4 | + | + | + | + | + | + | + |
| 5 | + | + | − | − | − | − | − |
| 6 | + | + | + | + | + | + | + |
| 7a | + | + | + | + | + | + | − |
| 7b | − | + | − | − | − | − | − |

Table 9 legend
TDLN refer to individual patient nodes examined (a and b refer to two separate nodes). Pathology refers to the hematoxylin and eosin staining histopathology analysis of lymph node sections. + refers to presence of melanoma metastases and − refers to no metastases. RT-PCR analysis detected by Etbr and Southern blot is indicated as + or −. Tyr refers to RT-PCR analysis by tyrosinase primers followed by nested tyrosinase RT-PCR if negative.

In conclusion, β-HCG is a useful addition to the group of melanoma markers described in Examples I through V. The frequency of expression of β-HCG mRNA in melanoma appears to be similar to that of the melanoma tumor antigens MAGE-3 and MAGE-1.

EXAMPLE IX

DETECTION OF GALNAC MRNA EXPRESSION IN MELANOMA CELLS AND BIOPSIES

A. Materials and Methods (i) Melanoma Cell Lines and Surgical Specimens

Melanoma cell lines were all established at JWCI and grown as described in Example I. 20 melanoma tumor biopsy specimens were obtained as described in Example VII. RNA extraction and RT-PCR assay was as described in Example VI.

(ii) Oligonucleotide Primers and Probes

Oligonucleotide primers were synthesized and purified at the Molecular Biology Institute Core Facility, UCLA. The GalNAc primers used were:

5'-CCAACTCAACAGGCAACTAC-3' (SEQ ID NO: 19) and 3'

GATCATAACGGAGGAAGGTC-3' (SEQ ID NO: 20).

cDNA probes, amplified by PCR with these primers, were used in Southern blotting, which was performed as described in Example II. The tyrosinase and MAGE-3 primers were the same as described in Example I and β-HCG

TABLE 10

GaLNAc expression in melanoma biopsies and cell lines

| SPECIMENS | GalNAc EXPRESSION |
|-----------|-------------------|
| BIOPSIES# METASTASES | |
| 19 | − |
| 25 | − |
| 68 | − |
| 100 | + |
| 102 | + |
| 178 | − |
| 221 | − |
| 246 | + |
| 250 | − |
| 261 | − |
| 292 | + |
| 301 | + |
| 351 | + |
| 361 | + |
| 380 | + |
| 443 | + |
| MELANOMA CELL LINES | |
| MATT | + |
| M101 | + |
| M12 | + |
| M24 | + |
| M10 | + |
| M18 | + |
| MKN | + |
| MHL | + |
| MCE | + |
| MKE | + |
| MELL | + |
| MMAC | + |
| M18 | + |
| PERIPHERAL BLOOD LYMPOCYTES | |
| DONOR #1 | − |
| DONOR #10 | − |
| DONOR #12 | − |
| DONOR #13 | − |
| DONOR #322 | − |
| DONOR #323 | − |
| DONOR #324 | − |
| DONOR #325 | − |
| DONOR #326 | − |
| DONOR #338 | − |
| DONOR #339 | − |
| DONOR #340 | − |
| DONOR #342 | − |
| DONOR #343 | − |
| NORMAL LYMPH NODE #349 | − |
| NORMAL LYMPH NODE #364 | − |

B. Results

As shown in Table 7, detection of GalNAC mRNA was succesfully detected in 13 out of 14 melanoma cell lines and 10 out of 20 biopsy specimens. Furthermore, no GalNAc marker expression was observed in normal lymph nodes or PBL. These are similar results to those found for β-HCG and MAGE-3 in previous examples. Indicating that GalNAc mRNA expression is another marker which may be utilized for the detection of melanoma and metastases.

Amplification of GalNAc mRNA is an indicator of gangliosides, GM2 and GD2, expression. Direct detection of GM2 and GD2 in occult metastases and small tumor lesions such as melanoma primaries is very difficult and often impractical when using standard biochemical methods. Monoclonal antibodies to gangliosides are available but often cross-react with other carbohydrate structures and therefore are not reliable and do not represent absolute ganglioside expression (Hoon et al., 1993).

Detection of tumor cells with the marker GalNAc by RT-PCR provides a novel approach to detect metastatic melanoma and breast cancer cells in blood or fluids that would not be possible by current biochemical or immunological techniques.

EXAMPLE X

DETECTION OF β-HCG MRNA EXPRESSION IN BREAST CANCER CELLS

A. Materials and Methods (i) Breast Cell Lines

The established breast cancer cell line JWCI BM-1 was developed from a primary invasive ductal carcinoma tumor and characterized as a breast cancer line at the John Wayne Cancer Institute. Breast cell lines MDA-MB-231, MCF-7, BT-549, T-47D and BT-20 were obtained from the American Type Culture Collection (ATCC, Rockville, Md.) and were cultured according to instructions provided. The 734B line is an established subclone of MCF-7. Cells were grown in 10 k fetal calf serum (heat-inactivated) RPMI 1640 (Gemini Bioproducts, Calabasas, Calif.) plus penicillin and Streptomycin (GIBCO, Long Island, N.Y.) in T75 cm$^2$ flasks. Adherent cell lines were routinely passaged by trypsinization every 3–4 days. When cell lines attained 75–85% confluency they were used for PCR analysis.

(ii) RNA Preparation

Tri-Reagent (Molecular Research Center, Inc. Cincinnati, Ohio) was used to isolate total RNA from the cell lines and surgical specimens, following the manufacturer's instructions and described in Example I. One μg of total RNA was used in the PCR assay to detect β-HCG mRNA. Oligonucleotide primers and probes were as described in Example VI.

(iii) RT-PCR

Reverse transcription was as described in Example I, using oligo (dT)$_{(15)}$; and oligo nucleotides as described in Example VI.

The PCR mixture was also as described in Example I and incubated in an OmniGene temperature cycler (Hybaid, Middlesex, England) at 95° C. for 3 min for 1 cycle; 95° C. for 1 min, 65° C. for 1 min, 72° C. for 1 min for 30 cycles; and 72° C. for 10 min. The PCR cDNA products were assessed in a 2% agarose gel containing ethidium bromide. A 100 bp DNA ladder (GIBCO BRL Life Technologies Inc., Gaithersburg, Md.) was used as a bp reference marker. Restriction enzyme digestion and Southern blot analysis were performed as previously described in Example VI.

(iv) β-HCG Protein Expression in Breast Cancer Cells

Breast cancer cells from individual cell lines were seeded in 12 well tissue culture microplates at 2 million cells/well in 1.5 ml of RPMI 1640 without fetal calf serum and cultured at 37° C. in a tissue culture incubator for 24 hr. Supernatant was harvested and concentrated 10 times to a volume of 150 μl using Centricon 10 concentrators (Amicon Division, W.R. Grace & Co., Beverly, Mass.). β-HCG in the supernatant was measured using a total β-HCG Quantitative Test kit (Medix Biotech Inc., Foster City, Calif.), following the manufacturer's instructions. Supernatant samples were tested in duplicate with a standard reference for each assay. The ELISA reaction was read at 490 nm using a Vmax kinetic microplate reader (Molecular Devices Corp., Palo Alto, Calif.).

B. Results (i) β-HCG mRNA Expression in Breast Cell Lines

All seven breast cancer cell lines were found to express β-HCG mRNA. A positive result was indicated by a 367 bp cDNA band as detected by Etbr-staining and Southern blot analysis. To confirm the identity of the amplified PCR cDNA product, samples were digested with endonuclease Sty I. All seven -HCG PCR products were cleaved by Sty I to produce bands of 271 and 96 bp on Etbr gels, thus confirming β-HCG mRNA expression. As a negative control, PBL from 25 normal (male and female) volunteers were examined. None of the control specimens were shown to be positive for -HCG marker expression by PCR and Southern blotting.

The expression of α-HCG mRNA was also examined by PCR in breast cell lines. In cell lines MDA-MB-231, JWCI BM-1, and T-47D, α-HCG mRNA expression was detected by Etbr-stained gel electrophoresis. The α-subunit detected could be HCG or other related hormones since they all share a high degree of similarity in α-subunit. For this reason a-HCG as a cancer marker, is not practical.

(ii) β-HCG Protein Expression in Breast Cancer Cell Lines

Out of the seven breast cell lines expressing β-HCG mRNA, only three cell lines (MDA-MB-231, T47-D, JWCI BM-1) secreted detectable levels of β-HCG protein as analysed by ELISA (0.15 mIU, 0.15 mIU, 0.1 mIU/2×10$^6$ cells, respectively). The cell lines, producing β-HCG were those that were positive for α-HCG mRNA expression.

Breast cancer lines were also analysed for β-HCG receptor mRNA. Human β-HCG/LH receptor genes cloned recently, have been shown to possess a high degree of similarity (Minegish et al., 1990). All cell lines were positive for β-HCG/LH receptor mRNA expression. To evaluate whether β-HCG/LH receptor could be used as a marker for metastatic breast cancers, PBL from six normal volunteer donors (male and female) was analysed for the corresponding mRNA using the primers as described in Example VI. All donors expressed β-HCG/LH receptor mRNA indicating that the β-HCG/LH receptor is not a reliable marker for detecting breast cancer cells in blood or lymph nodes.

EXAMPLE XI

SENSITIVITY OF β-HCG MARKER

A. Materials and Methods (i) PCR Detection Sensitivity

The sensitivity of the PCR assay to detect β-HCG mRNA in breast cancer cells was assessed by the following methods:

(a) RNA was isolated from MDA-MB-231 cells and serially diluted from 1 to $10^{-6}$ μg, and then analysed by the RT-PCR assay.

(b) Cell suspension of MDA-MB-231 cells were prepared and diluted with PBL to produce an in vitro model occult carcinoma cells in lymph nodes. $10^7$ PBL were mixed with a variable number of cancer cells ranging from 1 to $10^5$. Total RNA was then isolated from the mixtures and analysed by the RT-PCR assay and observed on an Etbr gel along side a positive ($10^6$ MDA-MB-231 cells) and negative ($10^7$ PBL) control. All other method were as described in Example X. The PBL were obtained from normal volunteers in which PCR analysis had shown no presence of β-HCG mRNA.

B. Results

RT-PCR results of a series of diluted RNA isolated from MD-AMB-231 was determined on Etbr agarose gels. β-HCG marker was detected from as little as $10^{-5}$ μg RNA. This detection was enhanced ten fold by Southern blotting, enabling β-HCG mRNA expression detection from as little as $10^{-6}$ μg of RNA.

Employing the in vitro model it was shown that one breast cancer cell, determined by the amplification of β-HCG marker, could be detected up to among $10^7$ PBL.

EXAMPLE XII

DETECTION OF β-HCG MRNA EXPRESSION IN BREAST CANCER SPECIMENS

A. Materials and Methods (i) Surgical Specimens

Thirty-one lymph nodes were collected from 18 patients (13 invasive ductal carcinoma, 4 invasive lobular carcinoma, and one in situ carcinoma) who were undergoing mastectomy with axillary lymphadenectomy for clinically early stage breast cancer. Nodes that were only logistically practical for cutting, for conventional pathological diagnosis and for archive fixation were obtained for RT-PCR. Patients ranged in age from 37 to 73 years old. In order to compare the results of PCR with histological analysis, the lymph nodes were divided into two, one half was analyzed by PCR and the other by histopathological H & E staining of serial sections.

For a negative control, blood was obtained from 25 normal volunteer donors (both male and female). All further materials and methods were as described in previous examples.

B. Results

Table 11 shows the results of β-HCG mRNA expression in TDLN. Two TDLN from eleven patients (patient G to Q) and three TDLN from one patient were analysed. Five of the TDLNs were found to be negative by conventional H & E staining, were found to be positive for β-HCG marker expression in the PCR assay (No. 4, 16, 19, 23, and 24). If the RT-PCR assays were found to be negative, Southern blot analysis was subsequently performed.

Overall, 9 out of 31 TDLN were found to be negative by H & E staining and PCR with or without Southern blotting. Four of the TDLN which were found to be negative by both PCR and histological examination, were subsequently found to be positive following Southern blot analysis (No. 12, 13, 15, and 22). All 367 bp β-HCG PCR cDNA products detected by PCR or Southern blotting were digested by restriction enzyme Sty I. There were no TDLN found to be positive by histological examination, but found negative by PCR or PCR and by Southern blotting.

TABLE 11

Detection for β-HCG expressing tumor cells in breast TDLN

| Specimen number | Patient | Tumor histology | Pathology | PCR | Southern blot |
|---|---|---|---|---|---|
| 1 | A | lobular | + | + | |
| 2 | B | ductal | + | + | |
| 3 | C | ductal | + | + | |
| 4 | D | in situ | + | + | |
| 5 | E | lobular | + | + | |
| 6 | F | ductal | + | + | |
| 7 | G | ductal | − | − | − |
| 8 | | | − | − | − |
| 9 | H | ductal | − | − | − |
| 10 | | | + | + | |
| 11 | I | ductal | − | − | |
| 12 | | | − | − | + |
| 13 | J | ductal | − | − | + |
| 14 | | | − | − | − |
| 15 | K | ductal | − | − | + |
| 16 | | | − | − | + |
| 17 | L | ductal | − | − | − |
| 18 | | | + | + | + |
| 19 | M | ductal | − | + | |
| 20 | | | + | + | |
| 21 | N | ductal | − | − | |
| 22 | | | − | − | − |
| 23 | O | ductal | − | + | + |
| 24 | | | − | + | |
| 25 | P | ductal | + | + | |
| 26 | | | + | + | |
| 27 | Q | ductal | − | − | − |
| 28 | | | − | − | − |
| 29 | R | lobular | + | + | |
| 30 | | | + | + | |
| 31 | | | + | + | |

Table 11 legend
Individual patients are labelled as A–R and numbers refer to individual TDLN. Tumor histology represents H & E staining diagnosed pathology. Pathology refers to diagnoses of + or − for breast cancer metastases. PCR results are indicated as + or − on Etbr gel electrophoresis analysis. Specimens negative for RT-PCR assay were subsequently Southern blotted with β-HCG cDNA probe. Southern blot analysis is indicated as + or −.

EXAMPLE XIII

DETECTION OF BREAST CANCER CELLS BY MULTIPLE MARKERS

A. Materials and Methods (i) Breast Cell Lines and Surgical Specimens

The breast cell line MDA-MB-231, MCF-7, BT-549, T-47D and BT-20 were obtained from the American Type Culture Collection (ATCC, Rockville, Md.) and were cultured according to instructions provided. The 734B line is an established subclone of MCF-7. Cells were grown as described in Example X. 11 breast cancer biopsies were extracted as described in Example XII. RNA extraction and RT-PCR assay were as described in Example X.

(ii) Oligonucleotide Primers and Probes

Oligonucleotide primers were synthesized and purified at the Molecular Biology Institute Core Facility, UCLA. The MAGE-1 primer sequences were as follows: 5' primer was 5'GCTGGAACCCTCACTGGGTTGCC-3' (SEQ ID NO: 23) and the 3' primer was 5'-CGGCCGAAGGAACCTGACCCAG-3' (SEQ ID NO: 24). The RT-PCR cDNA product was 421 bp. The tyrosinase and MAGE-3 primers were the same as described in Example I, β-HCG primers were the same as described in Example VI and GalNAc primers were the same as described in Example IX. cDNA probes, amplified by PCR with these primers, were used in Southern blotting, which was performed as described in Example II.

B. Results

Multiple markers were used to analyse breast cancer cells and breast cancer biopsy specimens by RT-PCR and Southern blotting. Tables 12 and Table 13 shows the results. All breast cancer cells were positive for at least five, out of the six, markers. For the biopsy specimens, at least one of the markers were detected from all samples. None of the markers alone would have been able to detect cancer cells in all of the specimens. This variation in marker detection reflects the heterogeniety of tumor cells. In conclusion, multiple markers are more sensitive to detection of breast cancer than any one marker.

TABLE 12

Analysis of Markers in Breast Cancer Cell Lines

|  | MAGE3 | MAGE 1 | MUC-18 | p97 | GalNAc | β-HCG |
|---|---|---|---|---|---|---|
| BT20 | + | + | + | − | + | + |
| BT549 | + | − | + | + | + | + |
| 902P | + | + | + | + | + | + |
| T47D | + | + | + | − | + | + |
| 734B/24 | + | + | + | + | + | + |
| 231/45 | − | + | + | + | + | + |
| MCF7 | + | + | + | + | + | + |

+/−: RT-PCR or Southern Blotting

TABLE 13

Analysis of Markers in Breast Cancer Biopsies

| Biopsy tumor or number | GalNAc | β-HCG | MUC 18 | P-97 | MAGE-3 | MAGE-1 |
|---|---|---|---|---|---|---|
| 0350T2A122794 | + | + | + | − | − | + |
| 0424T2A011795 | − | − | − | − | + | − |
| 6433T2A011895 | − | + | + | − | + | − |
| 044T2A012095 | − | − | − | − | + | − |
| 0460T2A012695 | − | + | + | − | + | + |
| 0498T2K020395 | − | − | + | − | − | − |
| 0500T2K020695 | − | − | + | + | + | − |
| 0506T2A020795 | + | + | + | + | − | + |
| 0520T2A020995 | − | − | + | − | − | + |
| 0522T2A020995 | − | − | + | − | − | − |
| 0525T2A020995 | − | − | + | + | − | − |

+/−: RT-PCR and Southera r Blotting

EXAMPLE XIV

DETECTION OF GALNAC AS A MARKER FOR METASTATIC MELANOMA

A. Materials and Methods (i) Cell Lines and Tumor Specimens

Thirteen melanoma cell lines were established and characterized as described in Tsuchida, T., Saxton, R. E., Morton, D. L., and Irie, R. F. Gangliosides of human melanoma. J. Natl. Cancer Inst., 78: 45–54, 1987; Hoon, D. S. B., Ando, I., Sviland, G., Tsuchida, T., Okun, E., Morton, D. L., and Irie R. F. Ganglioside GM2 expression on human melanoma cells correlates with sensitivity to lymphokine-activated killer cells. Int. J. Cancer, 43: 857–862, 1989; and Tsuchida, T., Saxton, R. E., Morton, D. L., and Irie, R. F. Gangliosides of human melanoma. Cancer, 63: 1166–1174, 1989. They were assessed for GalNAc mRNA expression. The cell lines were assessed at early passages, and grown in 10% heat-inactivated fetal calf serum (Gemini, Caiabasas, Calif.) RPMI 1640 plus penicillin and streptomycin. Total RNA was extracted from cells when cultures reached 70–80% confluency.

Melanoma biopsies were obtained from primary and metastatic lesions from multiple anatomical sites of different patients. All melanoma biopsy specimens were assessed to verify the presence of malignant melanoma. Metastatic melanoma in draining regional TDLN studied was obtained predominantly from axillary and groin regions. Melanoma TDLN were assessed by pathologists and defined as melanoma negative or positive by standard H & E staining and immunohistochemistry(anti-S100 polyclonal antibody) staining. Hoon, D. S. B., Wang, Y., Dale, P. S., Conrad, A. J., Schmid, P., Garrison, D., Kuo, C., Foshag, L. J., Nizze, A. J., and Morton, D. L. Detection of occult melanoma cells in blood with a multiple-marker polymerase chain reaction assay. J. Clin. Oncol., 13: 2109–2116, 1995. Neuroblastoma biopsy specimens were obtained from the Cooperative Human Tissue Network (Case Western Reserve University, Cleveland, Ohio) and were collected immediately after surgery and cryopreserved in liquid nitrogen. All specimens were verified by a pathologist.

(ii) Blood Collection

Ten ml of blood was collected in sodium citrate-containing tubes. When venipuncture was performed, the first several ml of blood was discarded to avoid skin plug contamination. The isolation of nucleated blood cells was achieved by using a density gradient solution (Dot Kit, NGI). Sarantou, T., Chi, D. D. J., Garrison, D. A., Conrad, A. J., Schmid, P., Morton, D. L., and Hoon, D. S. B. Melanoma-associated antigens as messenger RNA detection markers for melanoma. Cancer Res., 57: 1371–1376, 1997. This procedure allows a highly efficient recovery of cells from blood without red blood cell contamination. Collected cells from the blood were used for RNA isolation. Melanoma patients with different AJCC stage of disease were accrued for blood sample collection. Patients' clinical stage of melanoma disease at the time of blood draw was determined and recorded. Patients were clinically followed up. X-rays, MRI, CAT scans, and PET scans were evaluated for disease burden presence and progression. All blood samples were coded for a double-blind study. Thus, patient information, such as stage of disease, was not known by individuals performing the RT-PCR and Southern blot assays. Likewise, the assay results were not known by individuals assessing clinical information of patients studied.

(iii) RNA Extraction

Total cellular RNA from blood, biopsies and cell lines was extracted, isolated, and purified using Tri-Reagent according to the manufacturer's protocol (Molecular Research Center, Inc., Cincinnati, Ohio). Cells trom melanoma cell lines were washed in PBS, trypsinized, and collected from tissue culture flasks. Tissue biopsies collected from surgery were immediately processed for RNA or cryopreserved at −80° C. for processing at a later time. Biopsy specimens were minced in Tri-Reagent on ice. Cell lines and biopsy specimens were kept on ice when being processed. All RNA extraction was carried out in a designated sterile laminar flow hood with RNAse-free labware. Purified RNA was quantitated and assessed for purity by UW spectrophotometry. Moreover, isolation of RNA was assessed by RT-PCR and ethidium bromide staining gel electrophoresis for β-actin expression; RT-PCR and Southern blot assay results were not used when β-actin was assessed to be negative by ethidium bromide gel electrophoresis. Tissue processing, RNA extraction, RT-PCR assay set up, and post-RT-PCR product analysis were carried out in separate designated rooms and facilities to prevent cross-over contamination. To avoid potential post-PCR contamination, RNA extraction, RT-PCR, and Southern blot analysis were performed separately by different individuals.

(iv) RT-PCR and Southern Blot Assay

The RT-PCR assay was carried out as described in Hoon, D. S. B., Wang, Y., Dale, P. S., Conrad, A. J., Schmid, P., Garrison, D., Kuo, C., Foshag, L. J., Nizze, A. J., and Morton, D. L. Detection of occult melanoma cells in blood with a multiple-marker polymerase chain reaction assay. J. Clin. Oncol., 13: 2109–2116, 1995 and Sarantou, T., Chi, D. D. J., Garrison, D. A., Conrad, A. J., Schrnid, P., Morton, D. L., and Hoon, D. S. B. Melanoma-associated antigens as messenger RNA detection markers for melanoma. Cancer Res., 57: 1371–1376, 1997. Reverse transcription (RT) was perforniied on the amount of total RNA specified for Moloney murine leukemia virus reverse transcriptase (Promega, Madison, Wis.). The RNA was incubated in 70° C. for 5 mm and then put on ice before addition of RT reaction reagents. The RNA with RT reagents added was incubated at 37° C. for 2 h and followed by 95° C. for 5 min. All RT reactions were carried out with oligo dT priming to avoid transcription of spurious non-polyadenylated mRNA. The PCR conditions were set up as follow: 1 cycle of denaturing at 95° C. for 5 min followed by 35 cycles of 95° C. for 1 min, 65° C. for 1 min, and 72° C. for 1 min before a final primer sequence extension incubation at 72° C. for 10 min. RT-PCR conditions were set up in a Omni thermocycler (Hybaid, Middlesex, UK) or a robotic thermocycler (National Genetics Institute). Oligonucleotide primers were synthesized and purified at National Genetics Institute. Optimal primer sequences were designed for specific GalNAc mRNA detection. The GalNac primers used were 5'-CCA ACT CAA CAG GCA ACT AC-3' (SEQ ID NO: 25) and 5'-GAT CAT AAC GGA GGA AGG TC-3' (SEQ ID NO: 26), and the resulting GalNAc RT-PCR cDNA product was 230 bp. The tyrosinase primers used were 5'-TTG GCA GAT TGT CTG TAG CC-3' (SEQ ID NO: 7) and 5'-AGG CAT TGT GCA TGC TGC TT-3' (SEQ ID NO: 8) (23), and the resulting tyrosinase RT-PCR cDNA product was 284 bp. A purified fragment of the cDNA product amplified with respective primer sets was labeled with digoxigenin (Boehringer Mannheim, La Jolla, Calif.) and used as a cDNA probe in the automated Southern blot assay(National Genetics Institute).

The automated Southern blot assay system provides RT-PCR product verification, with the highest stringency in blotting and sensitivity. Any discrepancies or faint signals in Southern blotting were repeated for verification. In each experiment set-up, samples of RT-PCR reagents without mRNA and normal donor PBL RNA were used as negative controls throughout RT-PCR procedure. cDNA template for the cDNA probe and previously tested positive tumor lines or tumor biopsy specimens were included in the assay as positive RT-PCR controls. Southern blots were scanned on an electronic imager, recorded using computer software, and verified by at least two readers for positive and negative results. If any of the controls did not work, the results were discarded; and the assay was repeated. A positive result was recorded only after verification by Southern blotting. This highly stringent system with multiple controls was designed to perform routine analysis of large number of samples while maintaining high specificity and consistency.

(v) Ganglioside Analysis

Gangliosides were biochemically extracted, purified, and quantitated from cell lines. Purified human normal and melanoma gangliosides were used as standards. Individual ganglioside standards (varying concentrations were made to establish a standard curve) were prepared on high performance thin layered chromatography plates (HPTLC) (Merck, Darmstadt, Germany).

B. Results (i) GalNAc mRNA Expression by Cell Lines

Optimal and stringent RT-PCR conditions were established for GalNAc mRNA detection. PCR conditions were standardized and uniform throughout the studies. All 13 established melanoma cell lines assessed were shown to be positive for GalNAc mRNA expression. Two melanoma cell lines and a normal melanocyte cell line, of which GM2/GD2 expressions were negative and moderately positive, respectively, were only weakly positive for GalNAc mRNA. GM2 and GD2 expression levels of different cell lines and GalNAc mRNA detection in these cell lines are shown in Table 1. Melanocytes from a primary culture line have been shown to have weak or low levels of GM2/GD2. Primary melanocyte culture lines established usually require tumor promoters or specific growth medium. The culturing conditions can cause alterations in cell metabolisms, therefore primary melanocyte culture cells are not always true representative of "normal" in vivo cells.

All the melanoma cell lines were established from metastatic lesions, which generally express higher levels of gangliosides than primary melanoma biopsies. Melanoma lines were all derived from cutaneous melanomas except MAtt, which was from an ocular melanoma metastasis. The RT-PCR analysis is "semi-quantitative" as shown by the strength of the Southern blot detection signal. Cell lines with a higher level of GM2 and GD2 expression as assessed biochemically had a stronger RT-PCR cDNA product band.

(ii) GalNAc mRNA Detection Sensitivity

Nucleated blood cells extracted from 37 normal volunteer donors were assessed as negative controls. No GalNAc mRNA activity was detected of the normal donor blood cells RNA under the optimal conditions established with the melanoma cell lines. To assess the sensitivity of GalNAc mRNA detection levels, the total RNA from 5 million cells (cell line) or melanoma tissue was serially diluted, and RT-PCR and Southern blot analysis was performed. In general, GalNAc mRNA in amounts greater than 1 ng could be detected consistently.

To further determine the assay's sensitivity, an in vitro model consisted of known number of melanoma cells from cultured cell lines diluted in normal donor PBL (GalNAc mRNA negative) was analyzed. The RT-PCR and Southern blot assay can consistently detect one to five melanoma cells in approximately 20 million normal donor PBL using GalNAc mRNA as a detection marker.

(iii) GalNAc mRNA Expression by Primary and Metastatic Melanomas To further evaluate the significance of the GalNAc mRNA as a melanoma marker, we examined melanoma tumor biopsies of primary and metastatic lesions. Five out of nine (56%) primary melanoma biopsies were positive for GalNAc mRNA expression (Table 14). Assessment of melanoma metastatic lesions was divided into two categories: metastases to melanoma draining lymph nodes and metastases to other distal organs. Melanoma predominantly metastasizes to TDLN and then sequentially metastasizes to distant sites. Tumor metastasis to distant organ sites represents a more advanced stage of disease(AJCC Stage IV). GalNAc mRNA was detected in 16 of 25 (64%) TDLN (Table 14). All assessed TDLN specimens were verified by H & E or irnmunohistochemistry as positive for metastatic melanoma. Assessment of metastatic lesions to different organ sites demonstrated 14 of 23 (61%) positive for GalNAc mRNA (Table 14).

TABLE 14

Assessment of GalNAc-T mRNA expression in tumor specimens

| Specimens | Total | RT-PCR positive (%) |
|---|---|---|
| Melanomas | | |
| Primary | 9 | 5 (56) |
| TDLN metastases | 25 | 16 (64) |
| Distal organ metastases | 23 | 14 (61) |

TABLE 14-continued

Assessment of GalNAc-T mRNA expression in tumor specimens

| Specimens | Total | RT-PCR positive (%) |
|---|---|---|
| Other cancers | | |
| Neuroblastomas | 5 | 4 (80) |
| Astrocytomas | 3 | 3 (100) |
| Renal cell carcinomas | 3 | 2 (67) |

RT-PCR positive refers to RT-PCR and Southern blot positive. All specimens assessed were β-actin RT-PCR positive. All non-melanoma cancers were primary tumors.

For comparison and assay verification purposes, human tumor biopsies of neuroblastomas, astrocytomas, and renal cell carcinomas were assessed. All of these tumors are known to express GM2 and/or GD2. In particular, neuroblastomas have been well characterized to express high levels of GD2. Four of the five neuroblastoma biopsies expressed GalNAc mRNA (Table 14). All astrocytoma biopsies assessed expressed detectable GalNAc mRNA. Renal cell carcinoma biopsies assessed showed that two out of three samples expressed GalNAc mRNA.

(iv) GalNAc mRNA in Melanoma Patients' Blood

GalNAc mRNA expression in the blood samples of melanoma patients of different AJCC stages of disease and those of normal donors were assessed. AJCC staging was determined retrospectively after the blood draw for the assay. In 126 melanoma patient blood samples assessed, 44 (35%) were positive for GalNAc mRNA expression (Table 15). All normal donors (age and sex matched) were negative for GalNAc mRNA expression (Table 15). When samples were divided according to the patients' AJCC stage, GalNAc mRNA was detected in 0%, 35%, 42%, and 37%, in stage I, II, III, and IV respectively. GalNAc mRNA expression was significantly greater in AJCC II, III and IV patient blood than normal donor blood (p=0.0001 for all respective groups; Fisher's exact test). GalNAc mRNA expression was also significantly greater in AJCC stage II, III and IV patient blood versus AJCC stage I patient blood (p=0.025, p=0.006 and p=0.014, respectively).

TABLE 15

Assessment of GalNAc-T mRNA expression in blood samples

| Blood specimens | Number of patients | RT-PCR positive (%) |
|---|---|---|
| Normal donors | 37 | 0 |
| Melanoma patients | | |
| AJCC stage I | 11 | 0 |
| AJCC stage II | 26 | 9(35) |
| AJCC stage III | 48 | 20(42) |
| AJCC stage IV | 41 | 15(37) |
| All stages | 126 | 44(35) |

Melanoma patients bloods assessed by RT-PCR and Southern blotting. RT-PCR positive refers to RT-PCR and Southern blot positive for GalNAc-T mRNA. Stages of disease of patients refer to patients' stage of disease at the time of the blood draw.

Of the 126 patients' blood samples tested, 89 randomly selected samples were assessed for tyrosinase mRNA expression (Table 16). Tyrosinase mRNA is one of the major RT-PCR markers used in detecting melanoma cells in blood. Forty-six percent of the patients analyzed were positive for tyrosinase mRNA expression while 37% of these patients were positive for GalNAc mRNA. The addition of GalNAc mRNA marker to tyrosinase mRNA marker increased sensitivity of melanoma detection in the assay by 21%. This suggested that either not all melanoma patients with circulating melanoma cells expressed tyrosinase. This may also indicate that tyrosinase and GalNAc mRNA expressions are independent of each other, without coordination.

TABLE 16

Tyrosinase and GalNAc-T mRNA expression in melanoma patients' blood

| AJCC stage | Tyrosinase (%) | GalNAc-T (%) | Tyrosinase or GalNAc-T (%) | Marker negative (%) |
|---|---|---|---|---|
| All stages n = 89 | 46(52) | 33(37) | 65(73) | 24(27) |
| AJCC Stage I & II n = 17 | 6(35) | 4(24) | 9(53) | 8(47) |
| AJCC Stage III n = 40 | 25(63) | 16(40) | 34(85) | 6(15) |
| AJCC Stage IV n = 32 | 15(47) | 13(41) | 22(69) | 10(31) |

RT-PCR and Southern blot analysis on patients' blood were performed to assess tyrosinase and GalNAc-T mRNA expression.

(v) GalNAc mRNA as a Tumor Progression Marker

GalNAc mRNA expression in melanoma patients blood was examined as a tumor progression marker. Tumor progression was defined as: cancer related death, new lesions, change in disease stage (i.e. AJCC stage II to IV), or change in clinically measurable tumor burden. Patients were followed-up after blood draw and assessed for clinical evidence of the above criteria. The clinical status at the time of the blood draw was considered as the base line. AJCC staging of 126 melanoma patients are listed in Table 15; of these, 17 patients showed change in disease status on clinical follow-up (Table 17). Majority (12/17, 71%) of these patients were GalNAc mRNA positive. The majority of these patients had their blood drawn within 8 months before onset of tumor progression. Interestingly, 3 of the patients (#6, #7, and #10) who had the longest time before change in clinical status were GalNAc mRNA negative. Of the 109 patients showing no clinical tumor progression at the time of follow up, 22 (20%) were GalNAc mRNA positive. Overall, there was a significant correlation (p<0.0001; Fisher's exact test) of GalNAc mRNA expression in blood of patients having immediate tumor progression.

TABLE 17

GalNAc mRNA as tumor progression marker in blood

| Patient | Status at blood draw | Status at FU | Time to change in status (mon) | GalNAc mRNA expression |
|---|---|---|---|---|
| 1 | cervical lymph nodes | >cervical lymph nodes | 7 | + |
| 2 | liver mets | >liver mets* | 8 | + |
| 3 | retroperitoneal mass | no progression* | 4 | − |
| 4 | AWD | no clinical change* | 1 | − |
| 5 | brain mets | >brain mets* | 7 | + |
| 6 | AWD | no clinical change* | 18 | − |
| 7 | AWD | no clinical change* | 10 | − |

TABLE 17-continued

GalNAc mRNA as tumor progression marker in blood

| Patient | Status at blood draw | Status at FU | Time to change in status (mon) | GalNAc mRNA expression |
|---|---|---|---|---|
| 8 | brain mets | >brain mets* | 8 | − |
| 9 | brain mets | >brain mets* | 8 | + |
| 10 | NED | no clinical change* | 10 | − |
| 11 | NED | satellite lesions | 3 | + |
| 12 | lung mets | >lung mets | 9 | + |
| 13 | lung mets | >lung mets | 6 | + |
| 14 | satellite lesions | >satellite lesions | 3 | + |
| 15 | lung mets | >lung mets | 1 | + |
| 16 | brain lesions | >brain lesions | 3 | + |
| 17 | satellite lesions | >satellite lesions | 3 | + |

Table 17 Legend
Patient clinical status and tumor burden were assessed on follow-up after blood procurement. Mean clinical follow up period was over 1 year. *, dead to follow-up. >, increase in tumor burden. Mets, metastasis.

EXAMPLE XV

STATISTICAL ANALYSIS OF MULTIPLE MARKER TESTS ON MELANOMA PATIENTS WITH NO CLINICAL EVIDENCE OF DISEASE 46 melanoma patients whose disease status were No Clinical Evidence of Disease (NED) were tested for the tumor markers tyrosinase, p97, Muc-18 and MAGE-3. The patients were followed for one year. In the first year following their marker tests, recurrence occurred to 8 patients at 84, 119, 160, 224, 281 322 and 367 days, respectively. All of them were AJCC stage III or IV patients and had 2 or more positive markers. One patient with stage III and a positive marker died due to heart attack four months after the tumor marker test. There was no evidence of disease at that time. The remaining 37 patients were still disease-free at the end of the year. Recurrence during the second year is shown below.

Number of positive markers and other covariates, such as AJCC stage, age, gender, depth of primary tumor were tested individually by Cox proportional hazard model to asses their effect on 1-year recurrence. All of these factors were included in the model simultaneously and stepwise procedure was used for covariate selection. A subgroup analysis was carried out for stage III and IV patients and the only one censored case was excluded. The Chi-square test was used to examine the correlation between tumor marker and one-year recurrence. Alpha level of 0.05 and two-sided tests were used for determination of statistical significance.

Results
1. Patient Characteristics

|  | NED | Recurrence in First Year |
|---|---|---|
| Gender |  |  |
| Male | 23 | 6 |
| Female | 15 | 2 |
| Age at the time of test |  |  |
| N | 38 | 8 |
| Mean ± SD | 54.2 ± 14.8 | 60.5 ± 12.0 |
| min.–max. | 27.4–74.1 | 43.4–78.1 |
| Breslow Depth of Primary Tumor |  |  |
| N | 31 | 8 |
| Mean ± SD | 2.54 ± 1.79 | 3.07 ± 3.04 |
| Clark Level |  |  |
| II | 4 | 1 |
| III | 8 | 4 |
| IV | 15 | 1 |
| V | 3 | 2 |
| unknown | 8 | 0 |
| AJCC Stage at the time of test |  |  |
| I | 1 | 0 |
| II | 11 | 0 |
| III | 19 | 2 |
| IV | 7 | 6 |
| # of Positive Markers |  |  |
| 0 | 3 | 0 |
| 1 | 12 | 0 |
| 2 | 11 | 2 |
| 3 | 11 | 6 |
| 4 | 1 | 0 |

2. AJCC Stage and # of Positive Markers

| Stage | 0–1 Markers | 2 Markers | 3–4 Markers |
|---|---|---|---|
| I–II | 7 | 3 | 2 |
| III | 7 | 7 | 7 |
| IV | 1 | 3 | 9 |

Chi-square test p = 0.04

3. Stage, Number of Positive Markers and Recurrence

| Stage | # of Positive Markers | # of NED Patients | # of Recurrence |
|---|---|---|---|
| I–III | 0–1 | 7 | 0 |
|  | 2–4 | 5 | 0 |
| III–IV | 0–1 | 8 | 0 |
|  | 2–4 | 18 | 8 |

4. Cox Proportional Hazard Model

No significant association of gender, age and Breslow depth of primary tumor with one-year recurrence was found in this study. Stage and number of positive markers were significantly related with recurrence when they were individually tested by Cox Proportional Hazard Model (likelihood ratio test p=0.004 and 0.039 respectively). When gender, age, stage, number of positive markers and interaction of stage and marker were all included in the model, only interaction of stage and marker was selected by the stepwise procedure.

| Variable | Parameter Estimate | Standard Error | Wald Test | Risk Ratio |
|---|---|---|---|---|
| Stage | 1.80 | 0.75 | p = 0.018 | 6.02 |
| Likelihood ratio test p = 0.004 | | | | |
| # of positive markers | 0.91 | 0.48 | p = 0.060 | 2.48 |
| Likelihood ratio test p = 0.039 | | | | |
| Stage*# of pos markers | 0.25 | 0.10 | p = 0.010 | 1.28 |
| Likelihood ratio test p = 0.008 | | | | |

When correlation of melanoma AJCC stage to multimarker expression (tyrosinase, p97, Muc-18, MAGE-3) in patients who tested positive for at least one marker were analyzed, significant difference (p<0.03) was observed when 2–4 markers positive were compared to one marker positive for AJCC stage III and IV individually. No significant difference was observed for the AJCC stage I/II patients.

The number of markers also correlated to disease free survival rate after one and two years as shown in FIG. 1.

The following data represents results after two years:

A. Patient Characteristics After Two Years.

| Patient Characteristics | | No Recurrence | Recurrence | Total |
|---|---|---|---|---|
| Gender | Male | 19 | 10 | 29 |
| | Female | 13 | 4 | 17 |
| Age* | <60 | 19 | 7 | 26 |
| | ≧60 | 13 | 7 | 20 |
| AJCC Stage * | I | 1 | 0 | 1 |
| | II | 10 | 1 | 11 |
| | III | 15 | 6 | 21 |
| | IV | 6 | 7 | 13 |

*Age/Stage at the time when specimen was obtained.

B. Number of Positive Markers

| #of Positive Markers | 0 | 1 | 2 | 3 | 4 |
|---|---|---|---|---|---|
| # | 3 | 12 | 13 | 17 | 1 |
| % | 6.5% | 26.1% | 28.3% | 36.9% | 2.2% |

| | # of positive markers by stage, gender and age | | | | | |
|---|---|---|---|---|---|---|
| | 0 marker | 1 marker | 2 markers | 3 markers | 4 markers | Total |
| Gender | | | | | | |
| F | 2 | 3 | 4 | 8 | 0 | 17 |
| M | 1 | 9 | 9 | 9 | 1 | 29 |
| Age | | | | | | |
| <60 | 1 | 7 | 10 | 8 | 0 | 26 |
| ≧60 | 2 | 5 | 3 | 9 | 1 | 20 |
| Stage | | | | | | |
| I | 0 | 0 | 1 | 0 | 0 | 1 |
| II | 1 | 6 | 2 | 2 | 0 | 11 |
| III | 1 | 6 | 7 | 7 | 0 | 21 |
| IV | 1 | 0 | 3 | 8 | 1 | 13 |
| Total | 3 | 12 | 13 | 17 | 1 | 46 |

No significant correlation between # of positive markers and gender (Wilcoxon Rank Sum test exact inference 2-siede p-value=0.70).

No significant correlation between # of positive markers and age (Spearman correlation coefficient=0.10, p=0.497).

There was a significant correlation between # of positive markers and stage (Spearman correlation coefficient=0.43, p=0.003).

Stage, gender, age and # of positive markers were simultaneously tested using Cox proportional Hazard model. Age was not selected by stepwise selection procedure.

| Covariate | Parameter Estimate | Standard Error | Wald Test | Risk Ratio |
|---|---|---|---|---|
| Gender (0 = female 1 = male) | 0.92 | 0.61 | p = 0.130 | 2.51 |
| Stage (0 = Stage I–II 1 = Stage III–IV) | 1.43 | 1.06 | p = 0.177 | 4.17 |
| # of Positive Markers (0 = 0–2 markers 1 = 3–4 markers) | 1.14 | 0.58 | p = 0.048 | 3.13 |

For patients with same stage and gender, the hazard rate for patients with 3–4 positive marker comparing to patients with 2 or less positive markers will be 3 times higher (95% confidence interval 1.01–9.70).

EXAMPLE XVI

DETECTION OF MICROMETASTASIS BY RT-PCR IN FROZEN SECTIONS OF SENTINEL NODES FROM PATIENTS WITH CLINICAL STAGE I MELANOMA

A. Materials and Methods

Regional lymph nodes remain the most common site of melanoma metastases. This study was undertaken to compare immunohistochemistry (IHC) and hematoxylin and eosin staining (H&E) with a multiple marker RT-PCR plus Sounthern blot assay to detect mRNA expression of Mart-1, tyrosinase, and Mage-3 in the frozen sections of sentinel nodes (SN) from 41 patients with clinical stage I melanoma.

Fifty-two SN were obtained from 41 melanoma patients. The SN were bivalved, and frozen-section slices were evaluated by RT-PCR and Southern blot assay as described in Sarantou, T., Chi, D. D. J., Garrison, D. A., Conrad, A. J., Schmid, P., Morton, D. L., and Hoon, D. S. B. Melanoma-associated antigens as messenger RNA detection markers for melanoma. Cancer Res., 57: 1371–1376, 1997. The remainder of the SN were evaluated by H&E, and if negative by IHC. Control donor peripheral blood lymphocytes and normal lymph nodes were negative for marker expression. An SN was considered positive by RT-PCR when two or more mRNA markers are expressed.

B. Results

Seven of nine (78%) of patients with metastases to the SN when tested by H&E/IHC expressed two or more markers and two of nine (22%) expressed less than two markers. Fourteen of 32 (44%) of patients without metastases to the SN when tested by H&E/IHC expressed two or greater markers and eighteen of 32 (56%) expressed less than two markers.

Analysis of 52 Frozen Section Sentinel Nodes from 41 Patients

|  | Number of Samples Testing Positive for Marker in RT-PCR Test | Number of Patients Testing Positive for Marker in RT-PCR Test |
| --- | --- | --- |
| MART-1 | 27 (52%) | 23 (56%) |
| MAGE-3 | 23 (44%) | 21 (51%) |
| Tyrosinase | 19 (36%) | 16 (39%) |

Multiple marker RT-PCR and Southern blot assay increases detection of occult metastases in 44% of patients when compared with conventional histopathology.

EXAMPLE XVII

DETECTION OF METASTASES IN SENTINEL LYMPH NODES OF BREAST CANCER PATIENTS BY MULTIPLE MARKER RT-PCR

This example demonstrates a multiple marker RT-PCR and Southern blot assay for detection of metastases in frozen section of sentinel lymph nodes from breast cancer patients. Selective lymph node dissection (SLND) was perform in 41 AJCC stage I-IIIA breast cancer patients and 57 sentinel nodes (SN) were excised. The SN, which is the first node in the lymphatic basin to receive metastases from the primary tumor, was identified using isosulfan blue dye. Hematoxylin and eosin (H&E), immunohistochemistry (IHC), and RT-PCR were performed on adjacent sections of the SN.

A. Materials and Methods (i) Breast Cell Lines

The breast cell lines MCF-7, BT-20, MDA-MB-231 were obtained from the atcc (Rockville, Md.) and cultured according to instructions. The 734B line is an established subclone of MCF-7. The established breast cancer cell lines JWCI BM-1 and JCI JM-1 were developed from primary invasive ductal cracinoma and characterized as a breast cancer cell line at the John Wayne Cancer Institute. All 6 cell lines were grown in RPMI 1640 (Gemini Bioproducts, Calabasas, Calif.) plus 10% fetal calf serum (heat inactivated), penicillin and streptomycin (GIBCO, Grant Island, N.Y.) in T75 cm$^2$ flask. Adherent cell lines were routinely passaged by trypsinization every 3–4 days.

(ii) Surgical Specimens and Blood Prepartion

Surgical specimens were obtained in consultation with the surgeon and pathologist. All tissues were collected and dissected under stringent sterile conditions to prevent RNA contamination. Representative samples of primary breast malignant tissues and the above mentioned breast cancer cell lines were positive controls for establishing the multiple marker assay. Lymph nodes from patients undergoing surgery for noncancer (i.e. herniorraphy, cholecystectomy) conditions served as negative controls (internal review board approval for human subject usage was obtained).

The multiple marker RT-PCR assay was used to assess the tumor status of 57 SN from 41 AJCC stage I-IIIA breast cancer patients. Each SN was bisected; six 12 $\mu$g frozen section slices were obtained from each half of the SN. These were immediately stored at −80° C. until used for further examination by RT-PCR plus Southern blot assay. The remainder of the SN was examined with conventional H&E staining and by IHC analysis when no tumor was detected by H&E. Anticytokeratin IHC was performed using an antibody cocktail (MAK-6, Ciba-Corning, Alameda, Calif.) to low and intermediate molecular weight cytokeratins with an automated immunoperoxidase system (Ventana ES; Ventana Medical Systems, Inc. Tucson, Ariz.).

Ten milliliters of blood were collected in sodium citrate-containing tubes. The blood was centrifuged using a density gradient solution (National Genetics Institute, Los Angeles, Calif.) and nucleated cells in the blood were collected for RNA isolation. Blood cells from healthy donor volunteers served as negative controls.

TRI-REAGENT (Molecular Research Center, Cincinnati, Ohio) was used to isolate total RNA from the cell lines and frozen section SN, following the manufacturer's instructions. The sample was stored at −4° C. for 12 hr. after adding 500 $\mu$l of isopropranol for precipitation. The tube was then centrifuged at 14,000 g at 4° C. for 10 min. The sample was washed with 75% ethanol, vacuum-dried and suspended in 10 mM Tris-HCl with 0.1 EDTA solution (pH 8). The concentration, purity, and amount of total RNA were determined by UV spectrophotometry. The integrity of all RNA samples were determined by performing RT-PCR for $\beta$-actin mRNA expression, and assessment by ethidium bromide gel electrophoresis. Tissue processing, RNA extraction, RT-PCR assay set up and post-PCR product analysis were carried out in separate designated rooms in separate facilities to prevent cross-contamination.

(iii) RT-PCR and Southern Blot Assay

The RT-PCR assay was carried out as described in Sarantou, T., Chi, D. D. J., Garrison, D. A., Conrad, A. J., Schmid, P., Morton, D. L., and Hoon, D. S. B. Melanoma-associated antigens as messenger RNA detection markers for melanoma. Cancer Res., 57: 1371–1376, 1997. Reverse transcription (RT) was performed on the amount of total RNA specified for Moloney murine leukemia virus reverse transcriptase (Promega, Madison, Wis.). The RNA was incubated at 70° C. for 5 min and then put on ice befroe addition of RT reaction reagents. The RNA with RT reagents added was incubated at 37° C. for 2 hrs, followed by heating at 95° C. for 5 min. All RT reactions were carried out with oligo dT priming to avoid transcription of spurious non-polyadenylated mRNA. The PCR conditions for GalNAc and p97 were set up as follows: 1 cycle of denaturing at 95° C. for 5 min followed by 35 cycles of 95° C. for 1 min, 65° C. for 1 min, and 72° C. for 1 min before a final primer sequence extension incubation at 72° C. for 10 min. The PCR conditions for C-Met were similar, except an annealing temperature of 60° C. was used. RT-PCR conditions were set up in an Omni Thermocycler (Hybaid, Middlesex, UK). Oligonucleotide primers were synthesized and purified at National Genetics Institute. Optimal primer sequecnes were designed for specific C-Met, GalNAc, and p97 mRNA detection and cDNA products. Oligonucleotide 5' and 3' primers for individual markers were synthesized as follows: C-Met primers, 5'-GTC CTT TGG CGT CGT CCT CT-3' (SEQ ID NO: 27) and 5'ATG GGC GCA TTT CGG CTT TA-3' (SEQ ID NO: 28); GalNAc, 5' CAA ACT CAA CAG GCA ACT AC-3' (SEQ ID NO: 29) and 5'-GAT CAT AAC GGA GGA AGG TC-3' (SEQ ID NO: 26); p97, 5'-TAC CTG GTG GAG AGC GGC CGC CTC-3' (SEQ ID NO: 11) and 5'-AGC GTC TTC CCA TCC GTG T-3' (SEQ ID NO: 30). The RT-PCR cDNA products of C-Met, GalNAc, and p97 were 185, 230, and 286 base pairs, respectively. B-actin primers have been described in Hoon, D., Wang, Y., Dale, P., Conrad, A. J., Schimd, P., Garrison, D., Duo, C., Foshag, L. J., Nizzie, A. J., and Morton, D. L., Detection of occult melanoma cells in blood with a multiple-marker polymeras chain reaction assay. J. Clin. Oncol., 13:2109–2116, 1995. A purified fragment of the cDNA products amplified with respective primer sets was labeled with digoxigenin (Boehringer Mannheim, La Jolla, Calif.) and used as a cDNA probe in the automated Southern blot assay (National Genetics Institute).

Any discrepancies or faint signals in Southern blotting were repeated for verification. In each experiment set-up, samples of RT-PCR reagents without mRNA, donor PBL, and lymph node RNA from non-cancer patients were used as negative controls throughout RT-PCR procedures. Complementary DNA (cDNA) template for the cDNA probe and previously tested positive tumor lines or tumor biopsy specimens were included in the assay as positive RT-PCR controls. Southern blots were scanned on an electronic imager, recorded using computer software, and verified by at least two readers for positive and negative results. If known reagent control samples were different than expected, the results were discarded and the assay repeated with new reagents. A positive result was recorded only after verification by Southern blotting. This highly stringent system with multiple controls ws designed to perform routine analysis of large numbers of samples while maintaining high specificity and consistency.

B. Results (i) Marker Expression in Breast Cell Lines and Breast Tumors

All 6 breast cancer cell lines assessed expressed C-Met, GalNAc, and p97. Table 18. A positive result was indicated by an 185 base pair (bp) cDNA band as detected by EtBr for C-Met, 230 bp for GalNAc, and 286 bp for p97. Biopsies from ten primary infiltrating ductal carcinomas (IDC) were evaluated for mRNA tumor marker expression. GalNAc was expressed 6 of 10 (60%) primary breast tumors and C-Met and p97 were expressed in 7 of 10 (70%).

TABLE 18

RT-PCR & SOUTHERN BLOT ANALYSIS OF MRNA MARKER EXPRESSION

| | MRNA MARKER EXPRESSION | | |
|---|---|---|---|
| SPECIMEN | C-MET | GalNAc | P97 |
| BREAST CELL LINES (n = 6) | 6 (100) | 6 (100) | 6 (100) |
| BREAST TUMOR TISSUE (n = 10) | 7 (70) | 6 (60) | 7 (70) |
| HEALTHY DONOR PBL (n = 25) | 0 | 0 | 0 |
| NORMAL LYMPH NODES (n = 10) | 1 (10) | 0 | 1 (10) |
| SENTINEL LYMPH NODES (n = 57) | 43 (75) | 34 (60) | 36 (63) |

RT-PCR marker expression refers to RT-PCR and Southern blot positive. All specimens assessed were B-actin RT-PCR positive by EtBr analysis. () refers to % positive.

(ii) Marker Expression in Normal PBL and Lymph Nodes

PBL from 25 volunteer healthy donors were evaluated for mRNA marker expression. None of the markers were expressed in these 25 healthy donor PBL under the conditions described. The RT-PCR results were confirmed by EtBr and Southern blot assay.

After informed consent, ten normal lymph nodes (confirmed histopathologically), were obtained from patients undergoing non-cancer surgery (cholecystectomy, herniorraphy). No mRNA tumor marders were expressed in these normal lymph nodes by EtBr, but C-Met and p97 were expressed in 1 of 10 normal lymph nodes using southern blot analysis. GalNAc was not expressed in normal lymph nodes by EtBr or Southern blot assay.

(iii) mRNA Marker Detection Sensitivity

Total RNA was isolated from breast carcinoma cell lines and quantitated to determine the sensitivity of the assay. The total RNA was then serially diluted and RT-PCR and Southern blot was performed. RT-PCR was performed on serial dilution of RNA isolated from a representative breast cancer cell line, MCF-7. Detection of RT-PCR cDNA product could be detected by Southern blot analysis in $10^{-5}$ μg for C-Met and GalNAc, and $10^{-4}$ μg for p97. Most important is the amount of specific mRNA copy that can be detected.

(iv) Sentinel Marker Expression in Frozen Section Nodes

Fifty-seven SN from 41 AJCC stage I-IIIA breast cancer patients undergoing selective lymph node dissection (SLND) were analyzed by RT-PCR and Southern blot assay for C-Met, GalNAc, and p97 mRNA expression. Table 19. Seventeen of 57 SN (30%) contained metastases; 10 (18%) detected with H&E and an additional 7 (12%) with IHC. The remaining 40 of 57 (70%) DN did not contain detectable metastases. C-Met mRNA was expressed in 43 of 57 (75%) SN, GalNAc mRNA in 34 of 57 (60%), and p97 mRNA in 36 of 57 (63%).

TABLE 19

COMPARISON OF HISTOPATHOLOGY VERSUS MRNA EXPRESSION OF SN

| RT-PCR & SOUTHERN BLOT ANALYSIS OF mRNA MARKERS | PATHOLOGY OF SN BY H&E OR IHC | |
|---|---|---|
| | POSITIVE (%) | NEGATIVE (%) |
| C-MET | | |
| POSITIVE | 12 (71) | 31 (78) |
| NEGATIVE | 5 (29) | 9 (22) |
| GalNAC | | |
| POSITIVE | 13 (76) | 21 (53) |
| NEGATIVE | 4 (24) | 19 (47) |
| P97 | | |
| POSITIVE | 11 (65) | 25 (63) |
| NEGATIVE | 6 (35) | 15 (37) |

RT-PCR positive refers to RT-PCR and Southern blot positive. All specimens assessed were B-actin RT-PCR positive by EtBr analysis.

(v) Marker Expression in Sentinel Nodes Tumor-free by H&E and IHC

In 40 SN (Table 19) without metastases by conventional H&E or IHC staining, 31 of 40 (78%) expressed C-Met, 21 of 40 (53%) expressed GalNAc, and 25 of 40 (63%) expressed p97. Five of 40 SN (13%) expressed zero markers (Table 20), 10 of 40 (25%) expressed one marker, eight of 40 (20%) expressed two markers and 17 of 40 (42%) expressed all three mRNA markers. Twenty-five of 40 (62%) histopathology tumor-free SN expressed two or more markers.

TABLE 20

SENTINEL NODE RT-PCR & SOUTHERN BLOT MARKER EXPRESSION

| | RT-PCR AND SOUTHERN BLOT ANALYSIS NUMBER OF MARKERS | | | | |
|---|---|---|---|---|---|
| SENTINEL NODES (n = 57) | 0 (+) | 1 (+) | 2 (+) | 3 (+) | TOTAL |
| PATHOLOGY POSITIVE (n = 17) | 1 | 2 | 8 | 6 | 17 |
| PATHOLOGY NEGATIVE (n = 40) | 5 | 10 | 8 | 17 | 40 |

Pathology positive refers to H&E staining or IHC staining positive specimens.

(vi) Marker Expression in Sentinel Nodes with Tumor by H&E or IHC

In 17 SN that contained metases by conventional H&E staining or IHC, 12 of 17 (71%) expressed C-Met, 13 of 17

(76%) expressed GalNAc, and 11 of 17 (65%) expressed p97. No individual tumor marker alone was expressed in all 17 SN. One of 17 (6%) SN expressed 0 markers, 2 of 17 (12%) expressed 1 marker, 8 of 17 (47%) expressed 2 markers, and 6 of 17 (35%) expressed all three markers. Fourteen of 17 (82%) SN expressed 2 or more markers.

(vii) Heterogeneity of Marker Expression in Patients with Multiple Sentinel Nodes Eleven (27%) patients had more than one SN removed from their axillary basin. Table 21. In seven patients (64%), mRNA marker expression was the same (homogenous) (Patients 8–11). In 3 of these 4 patients, the histopathology varied between the multiple sentinel nodes, which could explain the difference in mRNA marker expression.

TABLE 21

MARKER EXPRESSION IN PATIENTS WITH MULTIPLE SENTINEL NODES

|  | H&E/IHC | C-Met | GalNAc | P97 |
|---|---|---|---|---|
| Patient 1 |  |  |  |  |
| SN(1) | − | + | + | + |
| SN(2) | − | + | + | + |
| Patient 2 |  |  |  |  |
| SN(1) | + | + | − | − |
| SN(2) | + | + | − | − |
| Patient 3 |  |  |  |  |
| SN(1) | − | + | + | + |
| SN(2) | − | + | + | + |
| Patient 4 |  |  |  |  |
| SN(1) | − | + | + | + |
| SN(2) | − | + | + | + |
| Patient 5 |  |  |  |  |
| SN(1) | − | + | − | − |
| SN(2) | − | + | − | − |
| Patient 6 |  |  |  |  |
| SN(1) | − | + | + | + |
| SN(2) | − | + | + | + |
| Patient 7 |  |  |  |  |
| SN(1) | − | − | + | + |
| SN(2) | − | − | + | + |
| SN(3) | − | + | + | + |
| Patient 8 |  |  |  |  |
| SN(1) | − | − | − | − |
| SN(2) | + | − | + | + |
| Patient 9 |  |  |  |  |
| SN(1) | + | + | + | − |
| SN(2) | − | + | − | − |
| SN(3) | − | + | − | − |
| Patient 10 |  |  |  |  |
| SN(1) | + | − | + | + |
| SN(2) | + | − | + | + |
| SN(3) | − | + | − | + |
| Patient 11 |  |  |  |  |
| SN(1) | + | + | − | + |
| SN(2) | + | + | − | − |

RT-PCR positive refers to RT-PCR and Southern blot positive. All specimens assessed were B-actin RT-PCR positive by EtBr analysis.

EXAMPLE XVIII

Melanoma Marker Test with Tyrosinase, MART-1, TRP-1, and MAGE-3

A. Material and Methods

Material and methods are as described in Example XVI.

B. Results

Melanoma Lymph Node Multi-Marker RT-PCR

| Markers | Tyrosinase | Mart-1 | TRP-1 | Mage 3 |
|---|---|---|---|---|
| +/(n) | 15(94) | 33(94) | 31(106) | 45(94) |

Examples of Marker Detection in Lymph Node Samples

| Sample No. | Tyrosinase | Mart-1 | TRP-1 | Mage 3 |
|---|---|---|---|---|
| 4093 | + | + | + | + |
| 5985 | − | + | + | − |
| 950 | − | − | + | + |
| 5432 | − | − | + | − |

Previous PCR studies have not analyzed large numbers of patients with different clinical stages of melanoma or breast cancer. This is important in evaluating the sensitivity and clinical significance of the assay. Furthermore, this information is useful in clinical staging disease into clinical subgroups, in particular, identifying subgroups of patients that need more intensive therapeutic intervention. For example, in NED patients with circulating tumor cells, immediate therapeutic intervention may be a very efficacious means of controlling potential tumor progression and, thus, preventing clinical disease. The detection of circulating cancer cells may also prove useful for monitoring a patient's response to operative and adjuvant therapies.

Applying a multiple melanoma marker method to the evaluation of circulating cancer cells also provides information about the tumor's phenotype. Identification of specific tumor-associated antigen(s) permits the rational use of specific immunotherapy protocols such as monoclonal antibodies and cancer vaccine (Hoon et al., 1993). The PCR assay also provides a rapid monitoring system as a follow-up to determine if a specific therapy is effective.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Acevedo, H. F., Krichevsky, A., Campbell-Acevedo, E. A., Gaylon, J. C., Buffor, M. J., and Hortsock, R. J. Flow cytometry method for the analysis of membrane-associated human chorionic gonadotropin, its subunits, and fragments on human cancer cells. *Cancer*, 69:1818–1828, 1992.

Agnantis, N J., Patra, F., Khaldi, L., and Filis, S T. Immunohistochemical expression of subunit beta HCG in breast cancer. *Eur. J. Gynaec. Oncol.*, 13:461–466, 1992.

Alfthan, H., Haglund, C., Roberts, P., and Stenman, U. H. Elevation of free S subunit of human choriogonadotropin and core β fragment of human choriogonadotropin in the serum and urine of patients with malignant pancreatic and biliary disease. *Cancer Res.*, 52:4628–4633, 1992.

American Joint Committee on Cancer, *Manual for Staging Cancer*, Fourth Ed., Lippincott & Co., Philadelphia, Pa.

Ando, I., Hoon, D. B., Suzuki, Y., Saxton, R. L., Golub, S. H. and Irie, R. F. Ganglioside GM2 on the K562 cell line is recognized as a target structure by human natural killer cells. *Int. J. Cancer* 40:12–17, 1987.

Balch C. M., Soong S. W., Shaw H. M, An analysis of prognostic factors in 4000 patients with cutaneous melanoma. *CUTANEOUS MELANOMA: CLINICAL MANAGEMENT AND TREATMENT RESULTS WORLDWIDE*, Balch C. M., Milton G. W. (eds.), Philadelphia, Pa., J. B. Lippincott Co. (1985), pp 321–352.

Bellus, D. How Do Specialty Polymers Modify the Chemical and Pharmaceutical Industries? *J. Macromolecular Science—Pure and Applied Chem*, A31(1):1355–1376, 1994.

Bettelheim, R., Price, K. N., Gelber, R. D., Davis, B. W., Cassigline, M., Goldrisch, A., Neville, A. M. Prognostic importance of occult axillary lymph node micrometastases from breast cancer. *Lancet*, 335:1565–1568, 1990.

Bo, M., and Boime, I. Identification of the transcription ally active genes of the chorionic gonadotropin S-gene cluster in vivo. *J. Biol. Chem.*, 267:3179–3184, 1992.

Boorstein, W. R., Vamvakopoulos, N. C. and Fiddes, J. C. Human, chorionic gonadotropin beta-subunit is encoded by at least eight genes arranged in tandem and inverted pairs. *Nature* (Lond.), 300:419–22, 1982.

Breslow, A., Thickness, cross-sectional area and depth of invasion in the prognosis of cutaneous melanoma. *Ann. Surg.* 172:902908, 1970.

Brown J. P., Nishiyama, K., Helistrom, I. Structural characterization of human melanoma-associated antigen p97 usinq monoclonal antibodies. *J. Immunol.* 127:539–546, 1981.

Burchill, S. A., Bradbury, M. F., Pittman, K., Southgate, J., Smith, B., Selby, P., Detection of epithelial cancer cells in peripheral blood by reverse transcriptase-polymerase chain reaction. *Brit. J. Cancer* 71:278–281, 1995.

Bystryn, J. C., Bernstein, P., Liu, P. Immunophenotype of human melanoma cells in different metastases. *Cancer Res.* 45: 56035607. 1985.

Cantor et al., *Genomics*, 13:1378, 1992.

Carubia, M. J., Yu, R. R., Macala, L. J. Kirkwood, J. and Varga, J. M. Gangliosides of normal and neoplastic human melanocytes. *Biochem. Biophys. Res. Commun.* 120:500–504, 1984.

Chen, Z. L., Wen, D. R., Coulson, W. F., Giuliano, A. E., and Cochran, A. J. Occult metastases in the axillary lymph nodes of patients with breast cancer node negative by clinical and histologic examination and conventional histology. *Disease Markers*, 9:239–248, 1991.

Clark, W. H. Jr., Elder, D. E., Guerry IV, D. et al. A study of tumor progression: The precursor lesions of superficial spreading and nodular melanoma. *Human Pathol.* 15:1147–1165, 1984.

Cole, L. A., Hartle, R. J., Laferla, J. J., and Ruddon, R. W. Detection of the free S-subunit of human chorionic gonadotropin (HCG) in cultures of normal and malignant trophoblast cells, pregnancy sera, and sera of patients with choriocarcinoma. *Endocrinology*, 113:1176–1178, 1983.

Datta, Y. H., Adams, P. T., Drobyski, W. R., Ethier, S. P., Terry, V. H. and Roth, M. S. Sensitive detection of occuli breast cancer by the reverse-transcriptase polymerase chain reation. *J. Clin. Oncol.* 12:475–482. 1994.

Davey et al., EPO No. 329 822.

Drmanac & Crkvenjakov. U.S. Pat. No. 5,202,231.

Edbooke et al., *EMBO J*. 4:715–724.

Elder, D. E., Rodeck, U., Thurin, J. Pigmented lesion-associated, antigens distinguish between benign and malignant melanocytic lesions. *Cancer Res.* 49: 5091–5096, 1989.

Erlich, H. A. (ed). *PCR TECHNOLOGY: PRINCIPLES AND APPLICATIONS FOR* nsm AMPT.TFTCATTnN Stnekton. New York, N.Y. (1989).

Fiddes, J. C., and Goodman H. M. Isolation, cloning and sequence analysis of the cDNA for the alpha-subunit of human chorionic gonadotropin. *Nature* (Lond.), 281:351–356, 1979.

Fidler, I. J. Critical Factors in the biology of human cancer metastasis: Twenty-eighth G. H. A. Clowes Memorial Award Lecture. *Cancer Res.* 50: 6130–6138, 1990.

Fidler, I. J. and Hart, I. R. Biologic diversity in metastatic neoplasms origins and implications. *Science* 217: 998–1001, 1982.

Fisher, E. R., Swarnidoss, S., Lee, C. H., Rockette, H., Redmond, C., and Fisher, B. Detection and significance of occult axillary node metastases in patients with invasive breast cancer. *Cancer*, 42:2025–2031, 1978.

Fitzpatrick, T. B. Skin Cancer. In: The American Cancer Society Cancer Handbook. Ch. 30, pp. 532–547, Doubleday & Co., Garden City, N.Y. (Arthur I. Holleb, M.D., ed.) 1986.

Forrest, A. P. Screening and breast cancer incidence. *J. Natl. Cancer Inst.*, 82:1525, 1990.

Friedman, L. S., Ostermeyer, E. A., Lynch, E. D., Szabo, C. I., Anderson, L. A., Dowd, P., Lee, M. K., Rowell, S. E., Boyd, J. and King, M. C. The search for BRAC1. *Cancer Res.*, 54:6374 6382, 1994.

Freifelder, D. Phpysical Biochemistry Applications to Biochemistry and Molecular Biology. 2nd ed. Wm. Freeman & Co., New York, N.Y. 1982.

Frohman, M. A., *PCR PROTOCOLS:A GUIDE TO METHODS AND APPLICATIONS*, Academic Press, N.Y. (1990).

Furukawa, K., Akagi, T., Nagata, Y., Yamada, Y., Shimotohno, K., Cheung, N-K, Shiku, H., Furukawa, K. GD2 ganglioside on human t-lymphotropic virus type I-infected T cells: Possible activation of -1,4-N-acetylgalactosaminyltransferase gene by p40tax. *Proc. Natl. Acad. Sci.* (USA) 90:1972–1976, 1993.

Gazdar et al., 1988. *Cancer Research* 48 :4078–4082.

Caugler, B., Van den Eynde, B., van der Bruggen, P. Human g AGE-3 codes for an antigen recognized on al melanoma auto-logous cytolytic T lymphocytes. *J. Exper. Med.* 179:9 930, 1994.

Gingeras et al., PCT Application WO 88/10315.

Giuliano, A. E., Kirgan, D. M., Guenther, J. M., and Morton, D. L. Lymphatic mapping and sentinel lymphadenectomy for breast cancer. *Ann. Surgery*, 220:391–401, 1994.

Giuliano, A. E., Breast. In: Tierney, L. M. Jr., McPhee, S. J., and Papadakis, M. A. (eds.) Current Medical Diagnosis and Treatment. 34th ed. pp.593–616 Appelton and Lange, Norwalk, Conn., 1995.

Giuliano, A. E., Breast Disease. in: J. S. Bereck and N. A. Haker (eds.) Practical Gynecological Oncology. pp.481–515. Williams & Wilkins, Baltimore, 1994.

Giuliano, A. E., Dale, P. S., Turner rr, and Morton, D. L., Improved axillary staging of breast cancer with sentinel lymphadenctomy. *Ann. Surg.* 222:394–401, 1995.

Giuliano, A. E., Jones, R. C., Brennan, M., and Statman, R., Sentinel lymphadenectomy in breast cancer. *J. Clin. Oncol.* 15:2345–2350, 1997.

Hainsworth, P. J., Tjandra, J. J., Stillwell, R. G., Machet, D., Henderson, M. A., Rennie, G. C., McKenzie, I. F. and Bennett R. C. Detection and significance of occult metastases in node negative breast cancer. *Br. J. Surg.*, 80:459–463, 1993.

Henderson, I. C. Adjuvant systemic therapy: Stage of the art, 1989. *Breast Cancer Res. Treat.*, 14:3–22, 1989.

Hoon, D. S. B., Hayashi, Y., Morisaki, T. Interleukin-4 plus tumor necrosis factor a augments the antigenicity of melanomacells. *Cancer Immunol. Immunother.* 37:378–384, 1993.

Hoon, D. S. B., Okun, E., Neuwirth, H., Morton, D. L., Irie, R. F. Aberrant expression of gangliosides in human renal cell carcinomas. *J. Urol.*, 150(6):2013–2018, 1993.

Hoon, D. S. B., Wang, Y., Sze L. Molecular cloning of a human monoclonal antibody reactive to ganglioside GM3 antigen on human cancers. *Cancer Res.* 53:5244–5250, 1993.

Hoon, D. S. B., Ando, I, Sviland, G., Tsuchida, T., Okun, E., Morton, D. L., and Irie, R. F. Ganglioside GM2 expression on human melanoma cells correlates with sensitivity to lymphokineactivated killer cells. *Int. J. Cancer* 43:857–862, 1989.

Hoon, D. S. B., Korn, E. L., and Cochran, A. J. Variations in functional immunocompetence of individual tumor-draining lymph nodes in humans. *Cancer Res.*, 47:1740–1744, 1987.

Hoon, D. S. B., Bowker, R. J, and Cochran, A. J. Suppressor cell, activity in human breast cancer draining lymph nodes. *Sur. Res: Comm.* 9:167–176, 1990.

Hoon, D. S. B., Banez, M., Okun, E., Morton, D. L., and Irie, R. F. Modulation of human melanoma cells by interleukin-4 and in combination with gamma interferon or a-tumor necrosis factor. *Csnewr Res.* 51:2002–2008. 1991.

Hoon, D. S. B., Sarantou, T., Fukashi, D., Chi, D. D. J., Kuo, C., Conrad, A. J., Schmid, P., Turner, R., and Guiliano, A. Detection of metastatic breast cancer by β-hCG polymerase chain reaction. *Int. J. Cancer (Pred. Oncol.)*; 69:369–374 (1996).

Innis et al., *PCR Protocols*, Academic Press, Inc., San Diego, Calif. (1990).

Irie, R. F., Tai, T. and Morton, D. L. Antibodies to tumor associated gangliosides (GM2 and GD2): Potential for suppression of melanoma recurrence. In: M. Torisu and T. Yoshida (eds), Basic mechanisms and clinical treatment of tumor metastasis, pp. 371–384, Academic Press, Tokyo, 1985.

Jacoby, D. R., Olding, L. B., Oldstone, M. B. A. Immunologic regulation of fetal-maternal balance. *Adv. Immunol.*, 35:157–208, 1984.

Jonas et al., 1985, *Proc. Natl. Acad. Sci. USA* 82:1994–1998.

Kaiser, H. E. Characteristics and pattern of direct tumor spreading. *LOCAL INVASION AND SPREAD OF CANCER*. K.W. Brunson (ed.), Netherlands, Kluwer Academic (1989), pp 1–16.

Kayser et al., 1988, *Pathology Research and Practice* 183 (4):412 417

Kayser et al., 1988, *Pathology Research Practice* 143:412417.

Khrapko et al., *J. DNA Sequencing Mapping* 1:375, 1991.

Konecki et al., 1987, *JBC* 262:17026–17030.

Kwoh et al., *Proc. Nat. Acad Sci.* USA 86:1173, 1989.

Kwon B. S., Haq A. K., Pomerantz S. H. Isolation and sequence of a cDNA clone for human tyrosinase that maps at the mouse calbino locus. *Proc. Nat'l Acad. Sci. USA* 84:773–7477, 1987. Kwon, B. S. Pigmentation genes: the tyrosinase gene family and the pmel 17 gene family. *J Invest. Dermatol*, 100(2 Suppl):134S140S, 1993.

Lagios, M. D., Westdahl. P. R., Margolin, F. R., and Rose, M. R. Duct carcinoma in situ. Relationship of extent of noninvaisve disease to the frequency of occult invasion, multicentricity, lymph node metastasis, and short-term treatment failures. *Cancer*, 50:1309–14, 1982.

Lehmann, J. M., Riethmuller, G., Johnson, J. P. MUC-18, a marker of, tumor progression in human melanoma, shows a sequence similarity to the neural cell adhesion molecules of the immunoglobulin superfamily. *Proc. Nat'l Acad. Sci. USA* 86:9891–9895, 1989.

Lehmann, J. M., Holzmann, B., Breitbart, E. W. Discrimination between benign and malignant cells of melanocytic lineage by two novel antigens, a glycoprotein with a molecular weight of 113,000 and a protein with a molecular weight of 76,000. *Cnnnor Rs.s* 47:841–845. 1987.

Madersbacher S, Kratzik C, Gerth R, Dirnhofer S and Berger P. Human chorionic gonadotropin (HCG) and its free subunits in hydrocele fluids and neoplastic tissue of testicular cancer patients: Insights into the in vivo hCG-secretion pattern. *Cancer Res.* 54:5096–5100, 1994.

Marcillac, I., Troalen, F., Bidart, J. M., Ghillani, P., Ribrag, V., Escudier, B., Malassagne, B., Droz, J. P., Lhomme, C., Rougier, P., Duvillard, P., Prade, M., Lugagne, P. M., Richard, F., Pynard, T., Bohuon, C., Wands, J., and Bellet, D. Free human chorionic gonadotropin-subunit in gonadal and nonqonadal neoplasms. *Cancer Res.*, 52:3901–3907, 1992.

Martin et al., Recent Progress in Hormone Research 45:467–506, 1989.

McManus, L M., Naughton, M A., and Martinez-Hernandez, A. Human chorionic gonadotropin in human neoplastic cell. *Cancer Res.* 36:3476–3481, 1976.

Miller et al., PCT Application WO 89/06700.

Minegish, T., Nakamura, K., Takakura, Y., Miyamoto, K., Hasegawa, Y., Ibuki, Y., and Igarashi, M. Cloning and sequencing of human LH/hCG receptor cDNA. *Biochem. Biophys. Res. Commun.*, 172:1049–1054, 1990.

Moertel, C. G., Fleming, T. R., MacDonald, J. S. An evaluation of the carcinoembryonic antigen (CEA) test for monitoring patients with resected colon cancer. *J. Amer. Med. Assoc.* 270:943–947, 1993.

Moreno, J. G., Croce, C. M., Fisher, R. Detection of hematogenous micrometastasis in patients with prostrate cancer. *Cancer Res.* 52:6110–6112, 1992.

Morisaki, T., Yuzuki, D. H., Lin, R. T. Interleukin 4 receptor expression and growth inhibition of gastric carcinoma cells by interleukin 4. *Cancer Res.* 52:6059–6065, 1992.

Morton, D. L., Wong, J. H., Kirkwood, J. M. Malignant melanoma in *CANCER MEDICINE* (3rd Ed.), Holland, J. F., Frei III, E., Bast Jr.,-C. C. (eds). Lea & Febiger, Philadelphia, Pa. (1993) pp. 1793–1824.

Morton, D. L., Davtyan, D. G., Wanek, L. A. Multivariate analysis of the relationship between survival and the microstage of primary melanoma by Clark's level and Breslow thickness. *Cancer* 71: 3737–3743, 1993.

Morton, D. L., Foshag, L. J., Hoon, D. S. B. Prolongation of survival in metastatic melanoma after active specific immunotherapy with a new polyvalent melanoma vaccine. *Ann. Surgery* 216:463–482, 1992.

Moyle, W. R. and Campbell, R. K. Gonadotropins. In: Endocrinology, 3rd ed., L. J. DeGroot et al (eds), Part II, Neuroendocrinology, W.B.Saunders Co., Philadelphia. pp. 230–241, 1993.

Mullis, K. B., Faloona, F. Specific synthesis of DNA in vitro via a polymerase-catalyzed chain reaction. *Methods Enzymol.* 155:335–350, 1987.

Nagata, Y., Yamashiro, S., Yodoi, J., Lloyd, K. O., Shiku, H. and Furukawa, K. Expression cloning of -1,4 Nacetylgalactosaminyltransferase cDNAs that determine the expression of GM2 and GD2 gangliosides. *J. Biol. Chem.* 267: 12082–12089, 1992.

Naito, H., Kuzumaki, N., Uchino, J. Detection of tyrosine hydroxylase mRNA and minimal neuroblastoma cells by the reverse trasncription-polymerase chain reaction. *Eur. J Cancer* 27: 762–765, 1991.

Natali et al., *Cancer* 59:55–63, 1987.

Neville, A. M., Price, K. N., Gelber, R. D., and Goldhirsch, A. Axillary node micrometastases and breast cancer. *Lancet*, 337: 1110, 1991.

Nicolson, G. L. Paracrine/autocrine growth mechanisms in tumor metastasis. *Oncology Res.* 4: 389–399, 1993.

NIH consensus Development Conference. NIH-Consensus Statement, 1992 Nordlund/J. J., Abdel-Malek, Z. A., Boissy, R. E. Pigment cell biology: an historical review. *J. Invest. Dermatol.* 92: 53S–60S, 1989.

Neville, A. M. Breast cancer micrometastases in lymph nodes and bone marrow are prognostically important. *Ann. Oncology*, 2:13–14, 1991.

Noguchi, S., Aihara, T., Nakamori, S., Motomura, K., Inaji, H., Imaoka, S., and Koyama, H. The detection of breast carcinoma micrometastases in axillary lymph nodes by means of reverse transcriptase-polymerase chain reaction. *Cancer*, 74:15951600, 1994.

Nowell, P. C. Genetic instability in cancer cells: relationship to tumor cell heterogeneity. *TUMOR CELL HETEROGENEITY*, Owens, A. H., Coffey, D. S., Baylin, S. B. (eds.). New York, Academic Press (1982) pp. 351–365.

Ohara et al., *Proc. Nat'l Acad. Sci. USA*, 86:5673–5677, 1989.

Oliver, R. T. D., Nouri, A. M. E., Crosby, D., Iles, R. L., Navarette, C., Martin, J., Bodmer, W., and Festenstein, H. Biological significance of beta hCG, HLA and other membrane antigen expression on bladder tumors and their relationship to tumor infiltrating lymphocytes (TIL). *J. Immunogenet.*, 16:381 –390, 1989.

Perez and Walker, 1990, *J. Immunol.* 142:3662–3667, and Bumal, 1988, Hybridoma 7(4):407–415.

Pierce, J. G. and Parsons, T. F. Glycoprotein hormones: structure and function. *Annu. Rev. Biochem.*, 50:465–495, 1981.

Ricketts, R M., and Jones, D B. Differential effect of human chorionic gonadotrophin on lymphocyte proliferation induced by mitogens. J. Reproductive Immunology, 7:225–232, 1985.

Rose, T. M., Plowman, G. D., Teplow D. B. Primary structure of the human melanoma-antigen p97 (melanotransferrin) deduced from the mRNA sequence. *Proc. Nat'l Acad Sci. USA* 83:1261–1265, 1986.

Rothman, P. A., Chao, V. A., Taylor, M. R., Kuhn, R. W., Jaffe, R. B. and Taylor, R. N. Extraplacental human fetal tissues express mRNA transcripts encoding the human chorionic gonadotropin-S subunit protein. *Mol. Reprod. Dev.* 33:1–6, 1992.

Russell et al., *Mol. Cell Endocrin.* 71(1):1–12, 1990.

Saiki, R. K., Gelfand, D. H., Stoffel, S., Scharf, S. J., Higuchi, R., Horn, G. T., Mullis, K. B., and Erlich, H. A. Primerdirected enzymatic amplification of DNA with a thermostable DNA polymerase. *Science*, 239:487–491, 1988.

Sambrook, J., Fritsch, E. F., Maniatis, T. (ed.). *MOLECULAR CLONING*. Cold Spring Harbor Lab. Press, Cold Spring Harbor, N.Y. (1989)

Scanlon and Strax. Breast Cancer. In: The American Cancer Society Cancer Book. Ch. 17, pp. 297–340, Doubleday & Co., Garden City, N.Y. (Arthur I. Holleb, M. D., ed.) 1986.

Sedmak, D. D., Meineke, T. A., and Knechtges, D. S. Detection of metastatic breast carcinoma with monoclonal antibodies to cytokeratins. *Arch. Pathol. Lab. Med.*, 113:786–789, 1989.

Selby, W. L., Mance, K. U., and Vork, H., CEA immunoreactivity in metastatic malignant melanoma. *Modern Path.* 5:415–419, Shuh, M. E., Nemoto, T., Penetrante, R. B., Rosner, D., and Dao T. L. Intraductal carcinoma. Analysis of presentation, pathologic findings, and outcome of disease. *Arch. Surgery*, 121:1303–1307, 1986.

Smart, C. R. Screening and early cancer detection. *Sem. Oncol.* 17:456–462, 1990. 25 Smith, B., Selby, P., Southgate, J. Detection of melanoma cells in peripheral blood by means of reverse transcriptase and solvmerase chain reaction. *Lancet* 338:1227–1229, 1991. Sobol et al., *Annals of Internal Medicine* 105(5):698700, 1986.

Southern, PCT Application No. WO 89/10977.

Southern et al *Genomics* 13:1008, 1992.

Spindel et al., *Proc. Natl. Acad. Sci. USA* 83:19–23, 1986.

Stamey, T. A., Kabalin, J. N., McNeal, J. E. Prostrate-specific antigen in the diagnosis and treatment of adenocarcinoma of the prostrate. *J. Urol.* 141:1076–1083, 1989.

Strezoska et al. *Proc Natl. Acad. Sci.* 88:10089, 1991.

Suva, *Gene* 77(1):95–105, 1989.

Talmadge, K., Vamvakopoulos, N. C. and Fiddes, J. C. Evolution of the genes for the S-subunit of human chorionic gonadotropin and luteinizinq hormone. *Nature*, 307:37–40, 1984.

Tormey, D. C., Waalkes, T. P., and Simon, R. M. Biological markers in breast carcinoma. II. Clinical correlations with human chorionic qonadotropin. *Cancer*, 39:2391–2396, 1977.

Tormey, D. C., Waalkes, T. P., Ahmann, D., Gehrke, C. W., Zunwatt, 3.W., Snyder, J., and Hansen, H. Biological markers in breast carcinoma. I. Incidence of abnormalities of CEA, HCG, three polyamines, and three minor nucleosides. *Cancer*, 35:1095–1100. 1975.

Torres, J. V., Yoshioka, N., and Atassi, M. Z. Antigenic regions on the S-chain of human chorionic gonadotropin and development of hormone specific antibodies. *Immunol. Invest.*, 16:607 618, 1987.

Tsuchida, T., Saxton, R. E. and Irie, R. F. Gangliosides of human melanoma: GM2 tumorigenicity. *J. Natl. Cancer Inst.* 78:4554, 1987.

Tsuchida, T., Saxton, R. E. and Irie, R. F. Gangliosides of human melanoma: GM2 tumorigenicity. *J. Natl. Cancer Inst.* 78:5560, 1987.

Vijayasardahi et al., *J. Experimental Medicine* 171(4) :1375–1380, 1990.

Walker et al., *Proc. Nat'l Acad. Sci. USA* 89:392–396, 1992. 25 Walker, M. J., Ronan, S. G., Han, M. C., Beattie, C. W. and Das Gupta, T. K. Interrelationship between histopathologic characteristics of melanoma and estrogen receptor status. *Cancer* 68:184–188. 1991.

Wu et al., *Genomics* 4:560, 1989.

Yamaguchi, A., Ishida, T., Nishimura, G., Kumaki, T., Katoh, M., Kosaka, T., Yonemura, Y., and Miyazaki, I. Human chorionic gonadotropin in colorectal cancer and its relationship to prognosis. *Br. J. Cancer*, 60:382–384, 1989.

Yoshimura, M., Nishimura, R., Murotani, A., Miyamoto, Y., Nakagawa, T., Hasegawa, K., Koizumi, T., Shii, K., Baba, S., and Tsubota, N. Assessment of urinary S-core fragment of human chorionic gonadotropin as a new marker of lung cancer. *Cancer*, 73:2745–2752, 1994.

What is claimed is:

1. A method of detecting metastatic melanoma cells in a patient comprising:
    (a) isolating nucleic acid from a biological sample of the patient;
    (b) amplifying nucleic acid targets, if present, from a set of melanoma marker genes which includes tyrosinase, MART-1, and MAGE-3; and
    (c) detecting the presence or absence of the nucleic acid targets;
        wherein the biological sample is taken from a compartment in which normal cells are negative for the melanoma marker genes and the presence of one or more nucleic acid target indicates the presence of metastatic melanoma cells.

2. The method of claim 1 wherein the nucleic acid is mRNA and further comprising the step of reverse transcribing the mRNA into DNA.

3. The method of claim 1 wherein the nucleic acid targets are amplified using polymerase chain reaction.

4. The method of claim 1 wherein the set of marker genes further includes TRP-1.

5. A method of detecting subclinical metastasis of melanoma cells comprising:
    (a) isolating nucleic acid from a biological sample of the patient;
    (b) amplifying nucleic acid targets, if present, from a set of melanoma marker genes which includes tyrosinase, MART-1, and MAGE-3; and
    (c) detecting the presence or absence of the nucleic acid targets thereby detecting subclinical metastasis of melanoma cells;
        wherein the biological sample is taken from a compartment in which normal cells are negative for the melanoma marker genes and the presence of one or more nucleic acid target indicates the presence of metastatic melanoma cells.

6. The method of claim 5 wherein the nucleic acid is mRNA and further comprising the step of reverse transcribing the mRNA into DNA.

7. The method of claim 5 wherein the nucleic acid targets are amplified using polymerase chain reaction.

8. The method of claim 5 wherein the set of marker genes further includes TRP-1.

9. A method of monitoring treatment of melanoma patients comprising:
    (a) isolating nucleic acid from a biological sample of the patient;
    (b) amplifying nucleic acid targets, if present, from a set of melanoma marker genes which includes tyrosinase, MART-1, and MAGE-3; and
    (c) detecting the presence or absence of the nucleic acid targets thereby monitoring treatment of melanoma patients;
        wherein the biological sample is taken from a compartment in which normal cells are negative for the melanoma marker genes and the presence of one or more nucleic acid target indicates the presence of metastatic melanoma cells.

10. The method of claim 9 wherein the biological sample is blood.

11. The method of claim 9 wherein the nucleic acid is mRNA and further comprising the step of reverse transcribing the mRNA into DNA.

12. The method of claim 9 wherein the nucleic acid targets are amplified using polymerase chain reaction.

13. The method of claim 9 wherein the set of marker genes further includes TRP-1.

14. A method of detecting metastatic breast cancer cells in a patient comprising:
    (a) isolating nucleic acid from a biological sample of the patient;
    (b) amplifying nucleic acid targets, if present, from a set of breast cancer marker genes which includes C-Met, GalNAc, MAGE-3, and CK20; and
    (c) detecting the presence or absence of the nucleic acid targets;
        wherein the biological sample is taken from a compartment in which normal cells are negative for the breast cancer marker genes and the presence of one or more nucleic acid target indicates the presence of metastatic breast cancer cells.

15. The method of claim 14 wherein the nucleic acid is mRNA and further comprising the step of reverse transcribing the mRNA into DNA.

16. The method of claim 14 wherein the nucleic acid targets are amplified using polymerase chain reaction.

17. The method of claim 14 wherein the set of marker genes further includes β-HCG.

18. A method of detecting subclinical metastasis of breast cancer cells comprising:
    (a) isolating nucleic acid from a biological sample of the patient;
    (b) amplifying nucleic acid targets, if present, from a set of breast cancer marker genes which includes C-Met, GalNAc, MAGE-3, and CK20; and
    (c) detecting the presence or absence of the nucleic acid targets thereby detecting subclinical metastasis of breast cancer cells;
        wherein the biological sample is taken from a compartment in which normal cells are negative for the breast cancer marker genes and the presence of one or more nucleic acid target indicates the presence of metastatic breast cancer cells.

19. The method of claim 18 wherein the nucleic acid is mRNA and further comprising the step of reverse transcribing the mRNA into DNA.

20. The method of claim 18 wherein the nucleic acid targets are amplified using polymerase chain reaction.

21. The method of claim 18 wherein the set of marker genes further includes β-HCG.

22. A method of monitoring treatment of breast cancer patients comprising:

(a) isolating nucleic acid from a biological sample of the patient;

(b) amplifying nucleic acid targets, if present, from a set of breast cancer marker genes which includes C-Met, GalNAc, MAGE-3, and CK20; and (c) detecting the presence or absence of the nucleic acid targets thereby monitoring treatment of breast cancer patients;

wherein the biological sample is taken from a compartment in which normal cells are negative for the breast cancer marker genes and the presence of one or more nucleic acid target indicates the presence of metastatic breast cancer cells.

23. The method of claim 22 wherein the nucleic acid is mRNA and further comprising the step of reverse transcribing the mRNA into DNA.

24. The method of claim 22 wherein the nucleic acid targets are amplified using polymerase chain reaction.

25. The method of claim 22 wherein the set of marker genes further includes β-HCG.

26. A kit for use in detecting melanoma cells in a biological sample comprising:

(a) pairs of primers for amplifying nucleic acids targets from a set of cancer marker genes which includes tyrosinase, MART-1 and MAGE-3; and (b) containers for each of the pairs of primers.

27. The kit of claim 26, further comprising enzymes and reagents for the preparation of cDNA's.

28. The kit of claim 27, further comprising enzymes and reagents for chromophoric labeling of nucleic acids.

29. A kit for use in detecting breast cancer cells in a biological sample comprising:

(a) pairs of primers for amplifying nucleic acids targets from a set of marker genes which includes C-Met, GalNAc, MAGE-3, and CK 20; and (b) containers for each of the pairs of primers.

30. The kit of claim 29, further comprising enzymes and reagents for the preparation of cDNA's.

31. The kit of claim 30, further comprising enzymes and reagents for chromophoric labeling of nucleic acids.

32. The kit of claim 29 where the marker genes are C-Met, GalNAc, MAGE-3, CK20 and β-HCG.

33. A method of detecting metastatic breast cancer cells in a patient comprising:

(a) isolating nucleic acid from a biological sample of the patient;

(b) amplifying nucleic acid targets, if present, from a set of cancer marker genes which includes C-Met, β-HCG, MAGE-3, and CK 20; and (c) detecting the presence or absence of the nucleic acid targets;

wherein the biological sample is taken from a compartment in which normal cells are negative for the breast cancer marker genes and the presence of one or more nucleic acid target indicates the presence of metastatic breast cancer cells.

34. The method of claim 33 wherein the nucleic acid is mRNA and further comprising the step of reverse transcribing the mRNA into DNA.

35. The method of claim 33 wherein the nucleic acid targets are amplified using polymerase chain reaction.

36. A method of detecting metastatic breast cancer cells in a patient comprising:

(a) isolating nucleic acid from a biological sample of the patient;

(b) amplifying nucleic acid targets, if present, from a set of cancer marker genes which includes β-HCG, GalNAc, MAGE-3, and CK 20; and (c) detecting the presence or absence of the nucleic acid targets;

wherein the biological sample is taken from a compartment in which normal cells are negative for the breast cancer marker genes and the presence of one or more nucleic acid target indicates the presence of metastatic breast cancer cells.

37. The method of claim 36 wherein the nucleic acid is mRNA and further comprising the step of reverse transcribing the mRNA into DNA.

38. The method of claim 36 wherein the nucleic acid targets are amplified using polymerase chain reaction.

39. A method of detecting metastatic breast cancer cells in a patient comprising:

(a) isolating nucleic acid from a biological sample of the patient;

(b) amplifying nucleic acid targets, if present, from a set of marker genes which includes β-HCG, MAGE-1, MAGE-3, and CK 20; and (c) detecting the presence or absence of the nucleic acid targets;

wherein the biological sample is taken from a compartment in which normal cells are negative for the breast cancer marker genes and the presence of one or more nucleic acid target indicates the presence of metastatic breast cancer cells.

40. The method of claim 39 wherein the nucleic acid is mRNA and further comprising the step of reverse transcribing the mRNA into DNA.

41. The method of claim 39 wherein the nucleic acid targets are amplified using polymerase chain reaction.

42. A method of detecting subclinical metastasis of breast cancer cells comprising:

(a) isolating nucleic acid from a biological sample of the patient;

(b) amplifying nucleic acid targets, if present, from a set of cancer marker genes which includes C-Met, β-HCG, MAGE-3, and CK 20; and (c) detecting the presence or absence of the nucleic acid targets thereby detecting subclinical metastasis of breast cancer cells;

wherein the biological sample is taken from a compartment in which normal cells are negative for the breast cancer marker genes and the presence of one or more nucleic acid target indicates the presence of metastatic breast cancer cells.

43. The method of claim 42 wherein the nucleic acid is mRNA and further comprising the step of reverse transcribing the mRNA into DNA.

44. The method of claim 42 wherein the nucleic acid targets are amplified using polymerase chain reaction.

45. A method of detecting subclinical metastasis of breast cancer cells comprising:

(a) isolating nucleic acid from a biological sample of the patient;

(b) amplifying nucleic acid targets, if present, from a set of cancer marker genes which includes β-HCG, GalNAc, MAGE-3, and CK 20; and (c) detecting the presence or absence of the nucleic acid targets thereby detecting subclinical metastasis of breast cancer cells;

wherein the biological sample is taken from a compartment in which normal cells are negative for the breast cancer marker genes and the presence of one or more nucleic acid target indicates the presence of metastatic breast cancer cells.

46. The method of claim 45 wherein the nucleic acid is mRNA and further comprising the step of reverse transcribing the mRNA into DNA.

47. The method of claim 45 wherein the nucleic acid targets are amplified using polymerase chain reaction.

48. A method of detecting subclinical metastasis of breast cancer cells comprising:
   (a) isolating nucleic acid from a biological sample of the patient;
   (b) amplifying nucleic acid targets, if present, from a set of cancer marker genes which includes β-HCG, MAGE-1, MAGE-3, and CK 20; and
   (c) detecting the presence or absence of the nucleic acid targets thereby detecting subclinical metastasis of breast cancer cells;
      wherein the biological sample is taken from a compartment in which normal cells are negative for the breast cancer marker genes and the presence of one or more nucleic acid target indicates the presence of metastatic breast cancer cells.

49. The method of claim 48 wherein the nucleic acid is mRNA and further comprising the step of reverse transcribing the mRNA into DNA.

50. The method of claim 48 wherein the nucleic acid targets are amplified using polymerase chain reaction.

51. A method of monitoring treatment of breast cancer patients comprising:
   (a) isolating nucleic acid from a biological sample of the patient;
   (b) amplifying nucleic acid targets, if present, from a set of cancer marker genes which includes C-Met, β-HCG, MAGE-3, and CK 20; and
   (c) detecting the presence or absence of the nucleic acid targets thereby monitoring treatment of breast cancer patients;
      wherein the biological sample is taken from a compartment in which normal cells are negative for the breast cancer marker genes and the presence of one or more nucleic acid target indicates the presence of metastatic breast cancer cells.

52. The method of claim 51 wherein the nucleic acid is mRNA and further comprising the step of reverse transcribing the mRNA into DNA.

53. The method of claim 51 wherein the nucleic acid targets are amplified using polymerase chain reaction.

54. A method of monitoring treatment of breast cancer patients comprising:
   (a) isolating nucleic acid from a biological sample of the patient;
   (b) amplifying nucleic acid targets, if present, from a set of cancer marker genes which includes β-HCG, GalNAc, MAGE-3, and CK 20; and
   (c) detecting the presence or absence of the nucleic acid targets thereby monitoring treatment of breast cancer patients;
      wherein the biological sample is taken from a compartment in which normal cells are negative for the breast cancer marker genes and the presence of one or more nucleic acid target indicates the presence of metastatic breast cancer cells.

55. The method of claim 54 wherein the nucleic acid is mRNA and further comprising the step of reverse transcribing the mRNA into DNA.

56. The method of claim 54 wherein the nucleic acid targets are amplified using polymerase chain reaction.

57. A method of monitoring treatment of breast cancer patients comprising:
   (a) isolating nucleic acid from a biological sample of the patient;
   (b) amplifying nucleic acid targets, if present, from a set of cancer marker genes which includes β-HCG, MAGE-1, MAGE-3, and CK 20; and
   (c) detecting the presence or absence of the nucleic acid targets thereby monitoring treatment of breast cancer patients;
      wherein the biological sample is taken from a compartment in which normal cells are negative for the breast cancer marker genes and the presence of one or more nucleic acid target indicates the presence of metastatic breast cancer cells.

58. The method of claim 57 wherein the nucleic acid is mRNA and further comprising the step of reverse transcribing the mRNA into DNA.

59. The method of claim 57 wherein the nucleic acid targets are amplified using polymerase chain reaction.

60. A kit for use in detecting breast cancer cells in a biological sample comprising:
   (a) pairs of primers for amplifying nucleic acids targets from a set of cancer marker genes which includes C-Met, β-HCG, MAGE-3, and CK 20; and
   (b) containers for each of the pairs of primers.

61. The kit of claim 60, further comprising enzymes and reagents for the preparation of cDNA's.

62. The kit of claim 61, further comprising enzymes and reagents for chromophoric labeling of nucleic acids.

63. A kit for use in detecting breast cancer cells in a biological sample comprising:
   (a) pairs of primers for amplifying nucleic acids corresponding to a set of cancer marker genes which includes β-HCG, GalNAc, MAGE-3, and CK 20; and
   (b) containers for each of the pairs of primers.

64. The kit of claim 63, further comprising enzymes and reagents for the preparation of cDNA's.

65. The kit of claim 64, further comprising enzymes and reagents for chromophoric labeling of nucleic acids.

66. A kit for use in detecting breast cancer cells in a biological sample comprising:
   (a) pairs of primers for amplifying nucleic acids targets from a set of cancer marker genes which includes MAGE-1, β-HCG, MAGE-3, and CK 20; and
   (b) containers for each of the pairs of primers.

67. The kit of claim 66, further comprising enzymes and reagents for the preparation of cDNA's.

68. The kit of claim 67, further comprising enzymes and reagents for chromophoric labeling of nucleic acids.

69. The method of claim 1 wherein the biological sample is selected from the group consisting of blood, tumor draining lymph node, bone marrow, and cerebrospinal fluid.

70. The method of claim 5 wherein the biological sample is selected from the group consisting of blood, tumor draining lymph node, bone marrow, and cerebrospinal fluid.

71. The method of claim 9 wherein the biological sample is selected from the group consisting of blood, tumor draining lymph node, bone marrow, and cerebrospinal fluid.

72. The method of claim 14 wherein the biological sample is selected from the group consisting of blood, tumor draining lymph node, bone marrow, and cerebrospinal fluid.

73. The method of claim 18 wherein the biological sample is selected from the group consisting of blood, tumor draining lymph node, bone marrow, and cerebrospinal fluid.

74. The method of claim 22 wherein the biological sample is selected from the group consisting of blood, tumor draining lymph node, bone marrow, and cerebrospinal fluid.

75. The method of claim 26 wherein the biological sample is selected from the group consisting of blood, tumor draining lymph node, bone marrow, and cerebrospinal fluid.

76. The method of claim 29 wherein the biological sample is selected from the group consisting of blood, tumor draining lymph node, bone marrow, and cerebrospinal fluid.

77. The method of claim 33 wherein the biological sample is selected from the group consisting of blood, tumor draining lymph node, bone marrow, and cerebrospinal fluid.

78. The method of claim 36 wherein the biological sample is selected from the group consisting of blood, tumor draining lymph node, bone marrow, and cerebrospinal fluid.

79. The method of claim 42 wherein the biological sample is selected from the group consisting of blood, tumor draining lymph node, bone marrow, and cerebrospinal fluid.

80. The method of claim 45 wherein the biological sample is selected from the group consisting of blood, tumor draining lymph node, bone marrow, and cerebrospinal fluid.

81. The method of claim 48 wherein the biological sample is selected from the group consisting of blood, tumor draining lymph node, bone marrow, and cerebrospinal fluid.

82. The method of claim 51 wherein the biological sample is selected from the group consisting of blood, tumor draining lymph node, bone marrow, and cerebrospinal fluid.

83. The method of claim 54 wherein the biological sample is selected from the group consisting of blood, tumor draining lymph node, bone marrow, and cerebrospinal fluid.

84. The method of claim 57 wherein the biological sample is selected from the group consisting of blood, tumor draining lymph node, bone marrow, and cerebrospinal fluid.

85. The method of claim 26 wherein the set of marker genes further includes TRP-1.

* * * * *